US012060320B2

(12) United States Patent
Podsiadlo et al.

(10) Patent No.: US 12,060,320 B2
(45) Date of Patent: Aug. 13, 2024

(54) ZEOLITE, PROCESS FOR MAKING SAME, AND USE THEREOF IN CONVERTING AROMATIC HYDROCARBONS

(71) Applicant: ExxonMobil Chemical Patents Inc., Baytown, TX (US)

(72) Inventors: Paul Podsiadlo, Humble, TX (US); Eric D. Metzger, Houston, TX (US); Wenyih F. Lai, Bridgewater, NJ (US); Ali A. Kheir, Houston, TX (US); Dominick A. Zurlo, Easton, PA (US); Jocelyn A. Gilcrest, Mullica Hill, NJ (US); Kathleen M. Keville, Beaumont, TX (US)

(73) Assignee: ExxonMobil Engineering & Technology Company, Baytown, TX (US)

( * ) Notice: Subject to any disclaimer, the term of this patent is extended or adjusted under 35 U.S.C. 154(b) by 199 days.

(21) Appl. No.: 17/434,237

(22) PCT Filed: Mar. 25, 2020

(86) PCT No.: PCT/US2020/024643

§ 371 (c)(1),
(2) Date: Aug. 26, 2021

(87) PCT Pub. No.: WO2020/205357

PCT Pub. Date: Oct. 8, 2020

(65) Prior Publication Data

US 2022/0144725 A1 May 12, 2022

Related U.S. Application Data

(60) Provisional application No. 62/826,317, filed on Mar. 29, 2019.

(30) Foreign Application Priority Data

Jul. 11, 2019 (EP) .................................... 19185757

(51) Int. Cl.

| | |
|---|---|
| ***C07C 5/27*** | (2006.01) |
| ***B01J 29/70*** | (2006.01) |
| ***B01J 35/61*** | (2024.01) |
| ***C01B 39/48*** | (2006.01) |

(52) U.S. Cl.

CPC ............. *C07C 5/2737* (2013.01); *B01J 29/70* (2013.01); *B01J 35/615* (2024.01); *C01B 39/48* (2013.01); *C01P 2002/60* (2013.01); *C01P 2006/12* (2013.01); *C07C 2529/70* (2013.01)

(58) Field of Classification Search

CPC ........... C07C 15/08; C07C 5/22; C07C 5/222; C07C 5/2708; C07C 5/2737; C07C 2529/40; C07C 2529/70; C07C 2529/80; C01P 2002/60; C01P 2006/12; Y02P 20/52; C01B 39/48; B01J 29/70; B01J 29/40; B01J 29/7038; B01J 29/80; B01J 2229/22; B01J 2229/36; B01J 2229/42; B01J 35/1019; B01J 35/0013; B01J 35/002; B01J 35/1057; B01J 35/1061

USPC ................. 585/410, 411, 414, 477, 480, 481

See application file for complete search history.

(56) References Cited

U.S. PATENT DOCUMENTS

| | | | | |
|---|---|---|---|---|
| 5,453,555 | A * | 9/1995 | Chang | C07C 2/864 585/446 |
| 5,689,027 | A | 11/1997 | Abichandani et al. | |
| 6,448,459 | B1 | 9/2002 | Magne-Drisch et al. | |
| 6,504,072 | B1 | 1/2003 | Brown et al. | |
| 6,689,929 | B2 | 2/2004 | Williams et al. | |
| 6,872,866 | B1 * | 3/2005 | Nemeth | C07C 5/2708 585/481 |
| 7,915,471 | B2 | 3/2011 | Leflaive et al. | |
| 8,697,929 | B2 | 4/2014 | Ou et al. | |
| 9,012,711 | B2 | 4/2015 | Ou et al. | |
| 9,156,749 | B2 | 10/2015 | Heeter et al. | |
| 9,205,401 | B2 | 12/2015 | Ou et al. | |
| 9,227,891 | B2 | 1/2016 | Leflaive et al. | |
| 9,249,068 | B2 | 2/2016 | Tinger et al. | |
| 9,260,355 | B2 | 2/2016 | Vermeiren et al. | |
| 9,295,970 | B1 | 3/2016 | Tinger et al. | |
| 9,302,953 | B2 | 4/2016 | Molinier et al. | |
| 9,321,029 | B2 | 4/2016 | Heeter et al. | |
| 9,434,661 | B2 | 9/2016 | Ou et al. | |
| 9,708,233 | B2 | 7/2017 | Molinier et al. | |
| 9,738,573 | B2 | 8/2017 | Molinier et al. | |
| 9,890,094 | B2 | 2/2018 | Kuzmanich et al. | |

(Continued)

FOREIGN PATENT DOCUMENTS

| | | | |
|---|---|---|---|
| CN | 104 549 440 | | 4/2015 |
| CN | 103 418 422 | | 6/2016 |
| CN | 103 418 423 | | 6/2016 |
| CN | 107 952 472 | | 4/2018 |
| CN | 105 817 261 | | 3/2019 |
| WO | 2000/010944 | | 3/2000 |
| WO | WO 2016/126443 | * | 8/2016 |

OTHER PUBLICATIONS

Machine Translation of CN 107952472, Apr. 24, 2018, pp. 1-20.*

(Continued)

*Primary Examiner* — Elizabeth D Wood

(57) ABSTRACT

Novel MEL framework type zeolites can be made to have small crystallite sizes and desirable silica/$SiO_2$ molar ratios. Catalyst compositions comprising such MEL framework type zeolites can be particularly advantageous in isomerization C8 aromatic mixtures. An isomerization process for converting C8 aromatic hydrocarbons can advantageously utilize a catalyst composition comprising a MEL framework type zeolite.

22 Claims, 8 Drawing Sheets

(56) References Cited

U.S. PATENT DOCUMENTS

| | | | |
|---|---|---|---|
| 10,010,878 | B2 | 7/2018 | Moscoso et al. |
| 10,058,854 | B2 | 8/2018 | Elia et al. |
| 10,118,165 | B2 * | 11/2018 | Lai ....................... B01J 29/7461 |
| 2002/0082462 | A1 | 6/2002 | Ferraro et al. |
| 2010/0179360 | A1 * | 7/2010 | Ichioka ................. C07C 5/2708 585/482 |
| 2011/0077146 | A1 * | 3/2011 | Whitchurch .......... C07C 5/2737 502/64 |
| 2011/0263918 | A1 | 10/2011 | Ou et al. |
| 2011/0319688 | A1 | 12/2011 | Ou |
| 2013/0274532 | A1 * | 10/2013 | Porter ....................... C07C 7/04 585/479 |
| 2014/0350316 | A1 | 11/2014 | Cao et al. |
| 2015/0376086 | A1 | 12/2015 | Tinger et al. |
| 2015/0376087 | A1 | 12/2015 | Molinier et al. |
| 2016/0101405 | A1 | 4/2016 | Tinger et al. |
| 2016/0185686 | A1 | 6/2016 | Molinier et al. |
| 2016/0257631 | A1 | 9/2016 | Kuzmanich et al. |
| 2016/0264495 | A1 | 9/2016 | Molinier et al. |
| 2017/0204024 | A1 | 7/2017 | Dreux et al. |
| 2017/0210683 | A1 | 7/2017 | Dreux et al. |
| 2017/0297977 | A1 | 10/2017 | Bambal et al. |
| 2018/0002252 | A1 * | 1/2018 | Salciccioli ................ C07C 7/12 |
| 2018/0362860 | A1 * | 12/2018 | McCarthy ................ B01J 29/48 |
| 2022/0134318 | A1 | 5/2022 | Lai et al. |

OTHER PUBLICATIONS

Zhang Lei et al: "Synthesis of Hierarchical Nano-MEL Zeolites with Controlled Sizes using Template-Free BEA Seeds for Oligomerization of Butene to Liquid Fuel with High Conversion Efficiency". Catalysis Communications, vol. 124, Feb. 26, 2019 (Feb. 26, 2019), pp. 36-40.

Lei Zhang et al: "Supporting Information on Synthesis of Hierarchical Nano-MEL Zeolites with Controlled Sizes using Template-Free BEA Seeds for Oligomerization of Butene to Liquid Fuel Feb. 26, 2019 (Feb. 26, 2019), pp. S-1, Materials Catalyst Preparation"; pp. S-2-S3, pp. S-6; figures S3-S5.

* cited by examiner

ZEOLITE, PROCESS FOR MAKING SAME, AND USE THEREOF IN CONVERTING AROMATIC HYDROCARBONS

CROSS-REFERENCE TO RELATED APPLICATIONS

This application is a US national phase application of PCT Application Serial No. PCT/US2020/024643 having a filing date of Mar. 25, 2020, which claims priority to and the benefit of U.S. Provisional Application No. 62/826,317 having a filing date of Mar. 29, 2019 and European Patent Application No. 19185757.2 having a filing date of Jul. 11, 2019, the disclosures of all of which are incorporated herein by reference in their entireties.

FIELD

This disclosure relates to zeolite materials, processes for making them, and use thereof in converting aromatic hydrocarbons. In particular, this disclosure relates to MEL framework type zeolite materials, processes for making them, and use thereof in isomerizing C8 aromatic hydrocarbons. This disclosure is useful, e.g., in processes for making xylenes, particularly p-xylene, including a step of isomerizing a mixture of C8 aromatic hydrocarbons in the presence of an isomerization catalyst, especially in liquid phase.

BACKGROUND

A high purity p-xylene product is typically produced by separating p-xylene from a p-xylene-rich aromatic hydrocarbon mixture comprising p-xylene, o-xylene, m-xylene, and optionally EB in a p-xylene separation/recovery system. The p-xylene recovery system can comprise, e.g., a crystallizer and/or an adsorption chromatography separating system known in the prior art. The p-xylene-depleted stream produced from the p-xylene recovery system (the "filtrate" from a crystallizer upon separation of the p-xylene crystals, or the "raffinate" from the adsorption chromatography separating system, collectively "raffinate" in this disclosure) is rich in m-xylene and o-xylene, and contains p-xylene at a concentration typically below its concentration in an equilibrium mixture consisting of m-xylene, o-xylene, and p-xylene. To increase yield of p-xylene, the raffinate stream may be fed into an isomerization unit, where the xylenes undergo isomerization reactions in contacting an isomerization catalyst system to produce an isomerized effluent rich in p-xylene compared to the raffinate. At least a portion of the isomerized effluent, after optional separation and removal of lighter hydrocarbons that may be produced in the isomerization unit, can be recycled to the p-xylene recovery system, forming a "xylenes loop."

Xylenes isomerization can be carried out under conditions where the C8 aromatic hydrocarbons are substantially in vapor phase in the presence of an isomerization catalyst (vapor-phase isomerization, or "VPI").

Newer generation technology have been developed to allow xylenes isomerization at significantly lower temperature in the presence of an isomerization catalyst, where the C8 aromatic hydrocarbons are substantially in liquid phase (liquid-phase isomerization, or "LPI"). The use of LPI vs. traditional VPI can reduce the number of phase changes (liquid to/from vapor) required to process the C8 aromatic feed. This provides the process with sustainability advantages in the form of significant energy savings. It would be highly advantageous for any p-xylene production plant to deploy a LPI unit, in addition to or in lieu of a VPI unit. For existing p-xylene production facilities lacking a LPI, it would be highly advantageous to add a LPI unit to compliment the VPI unit or replace the VPI unit.

Exemplary LPI processes and catalyst systems useful therefor are described in U.S. Patent Application Publication Nos. 2011/0263918 and 2011/0319688, 2017/0297977, 2016/0257631, and U.S. Pat. No. 9,890,094, the contents of all of which are incorporated herein by reference in their entirety. In the LPI processes described in these references, typically a MFI framework type zeolite (e.g., ZSM-5) is used as the catalyst.

Due to the many advantages of a LPI process and needs to deploy this technology, improvements in this technology, particularly the catalyst used, are also needed. This disclosure satisfies this and other needs.

References for citing in an Information Disclosure Statement (37 CFR 1.97(h)): W.O. 2000/010944; U.S. Pat. Nos. 5,689,027; 6,504,072; 6,689,929; U.S. Pub. No. 2002/0082462 A1; U.S. Pub. No. 2014/0350316 A1; U.S. Pub. No. 2015/0376086 A1; U.S. Pub. No. 2015/0376087 A1; U.S. Pub. No. 2016/0101405 A1; U.S. Pub. No. 2016/0185686 A1; U.S. Pub. No. 2016/0264495 A1; U.S. Pub. No. 2017/0210683 A1; US Patent Application Publication Nos. 2011/0263918; 2011/0319688; 2017/0297977; and 2016/0257631; U.S. Pat. Nos. 9,738,573; 9,708,233; 9,434,661; 9,321,029; 9,302,953; 9,295,970; 9,249,068; 9,227,891; 9,205,401; 9,156,749; 9,012,711; 7,915,471; and 9,890,094 and 10,010,878; 6,448,459; U.S. Pub. No. 2017/0204024 A1.

SUMMARY

It has been found, in a surprising manner that a novel class of MEL framework type zeolite can be made with very small crystallite size. The novel class of MEL framework type zeolite exhibits a surprisingly high performance when used in a C8 aromatics isomerization process operated in liquid phase ("LPI") as a catalyst. Such high performance includes one or more of a high isomerization activity, a low xylene loss, a low toluene yield, a low benzene yield, a low C9+ aromatics yield, and a high p-xylene selectivity, especially when compared to similar liquid-phase isomerization process utilizing a ZSM-5 zeolite as the catalyst. Very surprisingly, the high isomerization activity of this novel class of MEL framework type zeolite enables effective and efficient LPI of C8 aromatic hydrocarbons at an exceedingly high weight hourly space velocity ("WHSV"), such as 5 $hour^{-1}$ (and even 10 $hour^{-1}$) and greater, e.g., at ≥10 $hour^{-1}$, such as at even 15 $hour^{-1}$.

Thus, a first aspect of this disclosure relates to a zeolite material of the MEL framework type comprising a plurality of crystallites, wherein at least 75% of the crystallites have crystallite size of at most 200 nanometers, preferably at most 150 nanometers, preferably at most 100 nanometers, and more preferably at most 50 nanometers, as determined by transmission electron scope image analysis.

A second aspect of this disclosure relates to a process for making any of the zeolite material according to the first aspect of this disclosure, the process comprising: (I) forming a synthesis mixture from a silicon source, an aluminum source, an alkali metal (M) hydroxide, a source of a structure directing agent (SDA) selected from the group consisting of tetrabutyl ammonium ("TBA") compounds, alkyldiamines having 7-12 carbon atoms, and mixtures and combinations thereof, water, and optionally seed crystals, wherein the synthesis mixture has an overall composition having the following molar ratios:

$SiO_2$:$Al_2O_3$ 15-70

$OH^-$:Si 0.05-0.5

$M^+$:Si 0.2-0.4

SDA:Si 0.01-0.1

$H_2O$:Si 20

(II) subjecting the synthesis mixture to crystallization conditions which include heating the synthesis mixture at a temperature in the range of from 100° C. to 150° C. to form a reacted mixture comprising a solid material; and (III) obtaining the zeolite material from the reacted mixture.

A third aspect of this disclosure relates to a catalyst composition comprising any of the zeolite material according to the first aspect of this disclosure.

A fourth aspect of this disclosure relates to a process for converting a feed comprising C8 aromatic hydrocarbons, the process comprising: (I) feeding the aromatic hydrocarbon feed into a conversion reactor; and (II) contacting the C8 aromatic hydrocarbons at least partly in a liquid phase with a conversion catalyst composition comprising a MEL framework type zeolite in the conversion reactor under conversion conditions to effect isomerization of at least a portion of the C8 aromatic hydrocarbons to produce a conversion product effluent.

A fifth aspect of this disclosure relates to a process for converting a feed comprising C8 aromatic hydrocarbons, the process comprising: (I) feeding the aromatic hydrocarbon feed into a conversion reactor; and (II) contacting the C8 aromatic hydrocarbons substantially in liquid phase with a catalyst composition of any of B1 to B9 in the conversion reactor under conversion conditions to effect isomerization of at least a portion of the C8 aromatic hydrocarbons to produce a conversion product effluent, wherein the conversion conditions comprise an absolute pressure sufficient to maintain the C8 hydrocarbons in liquid phase, a temperature in the range from 150 to 300° C., and a WHSV in the range from 2.5 to 15.

DETAILED DESCRIPTION

Figure 1:
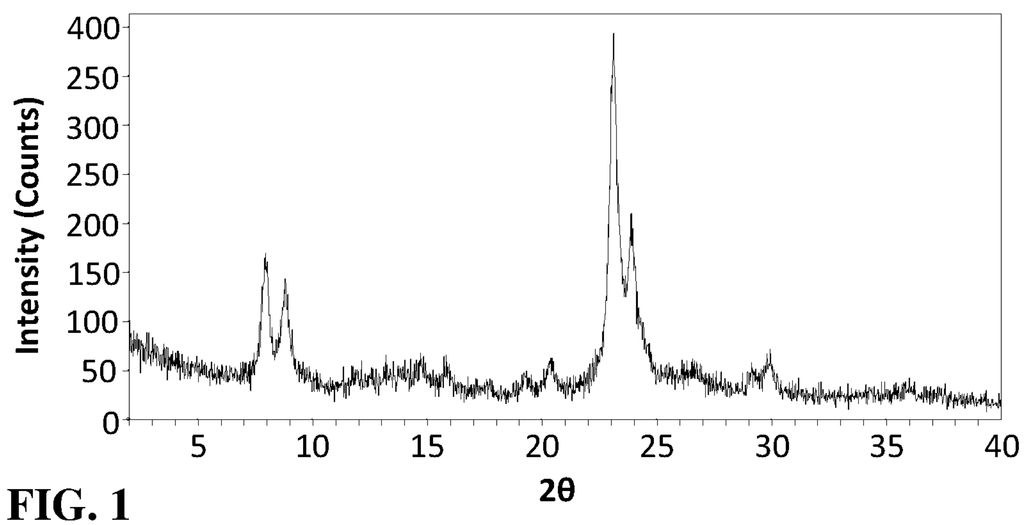
FIGS. 1, 2, and 3 are an X-ray diffraction ("XRD") graph, a scanning electron microscope ("SEM") image, and a transmission electron microscope ("TEM") image of a ZSM-11 zeolite synthesized in Example A1 of this disclosure, respectively.

In this disclosure, a process is described as comprising at least one "step." It should be understood that each step is an action or operation that may be carried out once or multiple times in the process, in a continuous or discontinuous fashion. Unless specified to the contrary or the context clearly indicates otherwise, multiple steps in a process may be conducted sequentially in the order as they are listed, with or without overlapping with one or more other step, or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step. Preferably, the steps are conducted in the order described.

Unless otherwise indicated, all numbers indicating quantities in this disclosure are to be understood as being modified by the term "about" in all instances. It should also be understood that the numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, embodiments using "an ether" include embodiments where one, two or more ethers are used, unless specified to the contrary or the context clearly indicates that only one ether is used.

"Consisting essentially of" as used herein means the composition, feed, or effluent comprises a given component at a concentration of at least 60 wt %, preferably at least 70 wt %, more preferably at least 80 wt %, more preferably at least 90 wt %, still more preferably at least 95 wt %, based on the total weight of the composition, feed, or effluent in question.

"Crystallite" means crystalline grain of a material. Crystallites with microscopic or nanoscopic size can be observed using microscopes such as transmission electron microscope ("TEM"), scanning electron microscope ("SEM"), reflection electron microscope ("REM"), scanning transmission electron microscope ("STEM"), and the like. Crystallites may aggregate to form a polycrystalline material.

For the purposes of this disclosure, the nomenclature of elements is pursuant to the version of Periodic Table of Elements as described in Chemical and Engineering News, 63(5), pg. 27 (1985).

The term "hydrocarbon" means (i) any compound consisting of hydrogen and carbon atoms or (ii) any mixture of two or more such compounds in (i).

The term "Cn hydrocarbon," where n is a positive integer, means (i) any hydrocarbon compound comprising carbon atom(s) in its molecule at the total number of n, or (ii) any mixture of two or more such hydrocarbon compounds in (i). Thus, a C2 hydrocarbon can be ethane, ethylene, acetylene, or mixtures of at least two of them at any proportion. A "Cm to Cn hydrocarbon" or "Cm-Cn hydrocarbon," where m and n are positive integers and m<n, means any of Cm, Cm+1, Cm+2, . . . , Cn−1, Cn hydrocarbons, or any mixtures of two or more thereof. Thus, a "C2 to C3 hydrocarbon" or "C2-C3 hydrocarbon" can be any of ethane, ethylene, acetylene, propane, propene, propyne, propadiene, cyclopropane, and any mixtures of two or more thereof at any proportion between and among the components. A "saturated C2-C3 hydrocarbon" can be ethane, propane, cyclopropane, or any mixture thereof of two or more thereof at any proportion. A "Cn+ hydrocarbon" means (i) any hydrocarbon compound comprising carbon atom(s) in its molecule at the total number of at least n, or (ii) any mixture of two or more such hydrocarbon compounds in (i). A "Cn− hydrocarbon" means (i) any hydrocarbon compound comprising carbon atoms in its molecule at the total number of at most it) n, or (ii) any mixture of two or more such hydrocarbon compounds in (i). A "Cm hydrocarbon stream" means a hydrocarbon stream consisting essentially of Cm hydrocarbon(s). A "Cm-Cn hydrocarbon stream" means a hydrocarbon stream consisting essentially of Cm-Cn hydrocarbon(s).

This disclosure provides a novel class of MEL framework type zeolite material, processes for making them, and uses of them in converting aromatic hydrocarbons such as isomerization of C8 aromatic hydrocarbons. This disclosure also relates to processes for converting aromatic hydrocarbons in the presence of the novel class of MEL framework type zeolite material, such as isomerization processes for converting C8 aromatic mixtures, particularly isomerization processes operated in liquid phase.

I. The Novel Class of MEL Zeolite Material of the First Aspect of this Disclosure The novel class of MEL framework type zeolite material of the first aspect of this disclosure comprises a plurality of primary crystallites. At least 75% (e.g., ≥80%, ≥85%, ≥90%, or even ≥95%) of the crystallites have crystallite size of ≤200 nanometer (e.g., ≤150, ≤100, ≤80, ≤50, ≤30 nanometers). Thus, e.g., at least 75% (e.g., ≥80%, ≥85%, ≥90%, or even ≥95%) of the crystallites can have a crystallite size in the range from cs1 to cs2 nanometers, where cs1 and cs2 can be, independently, 5, 10, 20, 30, 40, 50, 60, 70, 80, 90, 100, 120, 140, 150, 160, 180, 200, as long as cs1<cs2. Preferably cs1=10 and cs2=150. More preferably cs1=10 and cs2=50. In this disclosure, crystallite size is defined as the largest dimension of the crystallite observed under a transmission electron microscope ("TEM"). To determine crystallite size, a sample of the zeolite material is placed in a TEM, and an image of the sample is taken. The image is then analyzed to determine the crystallite size and distributions thereof. The small crystallite sizes of the MEL framework type zeolite material of this disclosure gives rises to surprisingly high catalytic activities and other performances, as discussed and demonstrated below.

Crystallites of the MEL framework type zeolite material of this disclosure can take various shapes such as substantially spherical, rod-like, and the like. The crystallites can have irregular shapes in TEM images. Thus, a crystallite may exhibit a longest dimension in a first direction ("primary dimension"), and a width in another direction perpendicular to the first direction ("secondary dimension"), where the width is defined as the dimension in the middle of the primary dimension, as determined by TEM image analysis. The ratio of the primary dimension to the width is called the aspect ratio of the crystallite. In certain embodiments, the crystallites can have an average aspect ratio determined by TEM image analysis in a range from ar1 to ar2, where ar1 and ar2 can be, independently, e.g., 1, 1.2, 1.4, 1.5, 1.6, 1.8, 2.0, 2.2, 2.4, 2.5, 2.6, 2.8, 3.0, 3.2, 3.4, 3.5, 3.6, 3.8, 4.0, 4.2, 4.4, 4.5, 4.6, 4.7, 4.8, and 5.0, as long as ar1<ar2. In certain embodiments, preferably ar1=1 and ar2=3. In certain embodiments, preferably ar1=1 and ar2=2.

The primary crystallites may have a narrow particle size distribution such that at least 90% of the primary crystallites by number have a primary crystallite size in the range of from 10 to 80 nm, preferably in the range of from 20 to 50 nm, as determined by analysis of images of the primary crystallites taken by TEM.

The small crystallites of the MEL framework type zeolite material of this disclosure can aggregate to form agglomerates. The agglomerates are polycrystalline materials having void space at the boundary of the crystallites. The MEL framework type zeolite of this disclosure can comprise agglomerates, typically irregular agglomerates. The agglomerates are formed from primary crystallites which can have an average primary crystallite size as determined by TEM image analysis of less than 80 nm, preferably less than 70 nm and more preferably less than 60 nm, for example, less than 50 nm.

Optionally, the primary crystallites of the MEL framework type zeolite can have an average primary crystallite size of less than 80 nm, preferably less than 70 nm, and in some cases less than 60 nm, in each of the a, b and c crystal vectors as measured by X-ray diffraction. The primary crystallites may optionally have an average primary crystallite size of greater than 20 nm, optionally greater than 30 nm, in each of the a, b and c crystal vectors, as measured by X-ray diffraction.

The MEL framework type zeolite of this disclosure may comprise a mixture of agglomerates of the primary crystallites together with some unagglomerated primary crystallites. The majority of the MEL framework type zeolite, for example, greater than 50 wt % or greater than 80 wt % can be present as agglomerates of primary crystallites. The agglomerates can be regular or irregular form. For more information on agglomerates please see Walter, D. (2013) Primary Particles-Agglomerates-Aggregates, in Nanomaterials (ed Deutsche Forschungsgemeinschaft (DFG)), Wiley-VCH Verlag GmbH & Co. KGaA, Weinheim, Germany. doi: 10.1002/9783527673919, pages 1-24.

Optionally, the MEL framework type zeolite of this disclosure can comprise ≥50 wt %, preferably ≥70 wt %, advantageously ≥80 wt %, more preferably ≥90 wt % and optionally substantially consists of said irregular agglomerates composed of primary crystallites having a primary crystallite size of ≤200 nm, preferably ≤180 nm, preferably ≤150 nm, preferably ≤120 nm, preferably ≤100 nm, preferably ≤80 nm, preferably ≤70 nm, preferably ≤60 nm, preferably ≤50 nm, for example ≤30 nm. Preferably, the MEL framework type zeolite of this disclosure comprises less than 10% by weight of primary crystallites having a size of >200 nm as determined by TEM image analysis. Preferably, the MEL framework type zeolite of this disclosure comprises less than 10% by weight of primary crystallites having a size of >150 nm as determined by TEM image analysis. Preferably, the MEL framework type zeolite of this disclosure comprises less than 10% by weight of primary crystallites having a size of >100 nm as determined by TEM image analysis. Preferably, the MEL framework type zeolite of this disclosure comprises less than 10% by weight of primary crystallites having a size of >80 nm as determined by TEM image analysis.

Preferably, said primary crystallites of the MEL framework type zeolite of the first and second aspects of this disclosure have an aspect ratio of less than 3.0, more preferably less than 2.0.

Said agglomerates of said primary crystallites are typically of irregular form in TEM images and may be referred to as being "secondary" particles because they are formed of agglomerates of the crystallites, which are the "primary" particles.

The MEL framework type zeolite material of this disclosure can in certain embodiments have a silica to alumina ratio of R(s/a) that can vary from r1 to r2, where r1 and r2 can be, independently, e.g., 10, 12, 14, 15, 16, 18, 20, 22, 24, 25, 26, 28, 30, 32, 34, 35, 36, 38, 40, 42, 44, 45, 46, 48, 50, 52, 54, 55, 56, 58, 60, as long as r1≤r2. In certain embodiments it is preferred that r1=20 and r2=50. In certain embodiments it is preferred that r1=20, and r2=40. In certain embodiments it is preferred that r1=20, and r2=30. Ratio r(s/a) can be determined by ICP-MS (inductively coupled plasma mass spectrometry) or XRF (X-ray fluorescence).

The MEL framework type zeolite material of this disclosure can in certain embodiments have a BET total specific surface area of A(st) that can vary from al to a2 $m^2/g$, where a1 and a2 can be, independently, e.g., 300, 320, 340, 350, 360, 380, 400, 420, 440, 450, 460, 480, 500, 520, 540, 550, 560, 580, 600, as long as a1<a2. In certain embodiments it is preferred that a1=400 and a2=500. In certain embodiments it is preferred that a1=400 and a2=475. A(st) can be determined by the BET method (Brunauer-Emmet-Teller method, a nitrogen adsorption method). The high total surface area A(st) of the zeolite material of this disclosure is another reason why it exhibits a high catalytic activity when used as a catalyst, such as a catalyst for converting aromatic hydrocarbons. The BET method can yield a total specific area of a measured material, including a microporous specific area component and a mesopore specific area component. The mesopore specific area may be called mesopore area, mesoporous area, or external area in this disclosure. The total specific area may be called total surface area or total area in this disclosure.

The MEL framework type zeolite material of this disclosure can in certain embodiments have a mesopore area of A(mp) that is ≥15% (e.g., ≥16%, ≥18%, ≥20%, ≥22%, ≥24%, ≥25%) of the total surface area A(st) discussed above. In certain embodiments it is preferred that A(mp)≥20%*A (st). In certain embodiments, it is preferred that A(mp) ≤40%*A(st). In certain embodiments, it is preferred that A(mp)≤30%*A(st). The high mesopore area A(mp) of the zeolite material of this disclosure is another reason why it exhibits a high catalytic activity when used as a catalyst, such as a catalyst for converting aromatic hydrocarbons. Without intending to be bound by a particular theory, it is believed that the catalystic sites present on the mesopore area of the zeolite material of this disclosure are more numerous due to the high mesopore area, which tend to contribute more to the catalytic activity than catalytic sites located in deep channels inside the zeolite material. The time required for reactant molecules to reach the catalytic sites on the mesopore surfaces and the product molecules to exit them is relatively short. Conversely, it would take significantly longer time for reactant molecules to diffuse into deep channels and for the product molecules to diffuse out of them.

The MEL framework type zeolite material of this disclosure can in certain embodiments have a hexane sorption value of v(hs) that can vary from v1 to v2 mg/g, where v1 and v2 can be, independently, e.g., 90, 92, 94, 95, 96, 98, 100, 102, 104, 105, 106, 108, 110, as long as v1<v2. Hexane sorption value can be determined by TGA (thermalgravimetric analysis) as is typical in the industry.

The MEL framework type zeolite material of this disclosure can in certain embodiments have an alpha value that can vary from a1 to a2, where a1 and a2 can be, independently, e.g., 500, 600, 700, 800, 900, 1000, 1200, 1400, 1500, 1600, 1800, 2000, 2200, 2400, 2500, 2600, 2800, 3000, as long as a1<a2. Alpha value can be determined by method described in U.S. Pat. No. 3,354,078 and Journal of Catalysis, Vol. 4, p. 527 (1965); vol. 6, p. 278 (1966) and Vol. 61, p. 395 (1980).

II. Process for Making the Novel Class of MEL Zeolite Material of the Second Aspect of this Disclosure Synthesis of molecular sieve materials typically involves the preparation of a synthesis mixture which comprises sources of all the elements present in the molecular sieve often with a source of hydroxide ion to adjust the pH. In many cases a structure directing agent (also known as a templating agent, or a template) is also present. Structure directing agents are compounds which are believed to promote the formation of molecular sieves and which are thought to act as templates around which certain molecular sieve structures can form and which thereby promote the formation of the desired molecular sieve. Various compounds have been used as structure directing agents including various types of quaternary ammonium cations.

The synthesis of molecular sieves is a complicated process. There are a number of variables that need to be controlled in order to optimize the synthesis in terms of purity, yield and quality of the molecular sieve produced. A particularly important variable is the choice of synthesis template (structure directing agent), which usually determines which framework type is obtained from the synthesis. Quaternary ammonium ions are typically used as the structure directing agents in the preparation of zeolite catalysts.

The "as-synthesised" molecular sieve will contain the structure directing agent in its pores, and is usually subjected to a calcination step to burn out the structure directing agent and free up the pores. For many catalytic applications, it is desired to convert the molecular sieve to the hydrogen form (H-form). That may be accomplished by firstly removing the structure directing agent by calcination in air or nitrogen, then ion exchanging to replace alkali metal cations (typically sodium cations) by ammonium cations, and then subjecting the molecular sieve to a final calcination to convert the ammonium form to the H-form. The H-form may then be subjected to various 'post-treatments" such as steaming and/or acid treatments to tailor the surface properties of the crystals. The products of such treatments are often referred to as "post-treated".

The present inventors have found that it is possible to prepare MEL framework type zeolite having a very small crystal size and having a high mesopore surface area, in particular by the selection of the synthesis mixture composition.

The structure directing agent ("SDA") is selected from the group consisting of TBA, alkyl diamines having 7-12 carbon atoms, and mixtures and combinations thereof. As used herein, "TBA" refers to the tetrabutyl ammonium cation. Examples of alkyl diamines having 7-12 carbon atoms include but are not limited to heptane-1,7-diamine, octane-1,8-diamine, nonane-1,9-diamine, decane-1,10-diamine, and undecane-1,11-diamine. Preferably, the structure directing agent is TBA. TBA can be included into the synthesis mixture as a halide, a hydroxide, any mixture thereof, or the like. TBA chloride, fluoride, bromide, iodide, or mixtures thereof, may be used. A preferred salt of TBA is TBA bromide, abbreviated as TBABr herein. Preferably, the molar ratio SDA:Si is in the range of from 0.005 to 0.20, more preferably from 0.01 to 0.10, especially from 0.02 to 0.05.

The molar ratio $Si:Al_2$ (also called silica to alumina or $SiO_2/Al_2O_3$ ratio) of the MEL framework type zeolite of this disclosure is preferably greater than 10 and may be in the range of, for example, from 10 to 60, preferably from 15 to 50, preferably from 15 to 40, preferably from 15 to 30, such as from 20 to 30, such as from 22 to 28. The ratio Si:$Al_2$ of the post-treated MEL framework type zeolite of this disclosure is preferably in the range of from 20 to 300, more preferably from 20 to 100.

Suitable sources of silicon (Si) include silica, colloidal suspensions of silica, precipitated silica, alkali metal silicates such as potassium silicate and sodium silicate, tetraalkyl orthosilicates, and fumed silicas such as Aerosil™ and Cabosil™. Preferably, the source of Si is a precipitated silica such as Ultrasil™ (available from Evonik Degussa) or HiSil™ (available from PPG Industries).

Suitable sources of aluminum (Al) include aluminum sulfate, aluminum nitrate, aluminum hydroxide, hydrated alumina such as boehmite, gibbsite and/or pseudoboehmite, sodium aluminate and mixtures thereof. Other aluminum sources include, but are not limited to, other water-soluble aluminum salts, or an aluminum alkoxide, such as aluminum isopropyloxide, or an aluminum metal, such as aluminum in the form of chips. Preferably, the aluminum source is sodium aluminate, for example an aqueous solution of sodium aluminate with a concentration in the range of 40 to 45%, or aluminum sulfate, for example an aluminum sulfate solution with a concentration in the range of from 45 to 50%.

Alternatively or in addition to previously mentioned sources of Si and Al, aluminosilicates may also be used as a source of both Si and Al.

Preferably, the Si:$Al_2$ ratio in the synthesis mixture is in the range of from 15 to 70, more preferably from 15 to 50, more preferably from 15 to 40, such as from 20 to 30.

The synthesis mixture also contains a source of alkali metal cation $M^+$. The alkali metal cation $M^+$ is preferably selected from the group consisting of sodium, potassium and mixtures of sodium and potassium cations. Sodium cation is preferred. Suitable sodium sources may be, for example, a sodium salt such as NaCl, NaBr or $NaNO_3$, sodium hydroxide or sodium aluminate, preferably sodium hydroxide or sodium aluminate. Suitable potassium sources may be, for example, potassium hydroxide or potassium halide such as KCl or KBr, or potassium nitrate. Preferably, the ratio $M^+$:Si in the synthesis mixture is in the range of from 0.1 to 0.5, more preferably from 0.2 to 0.4.

The synthesis mixture also contains a source of hydroxide ions, for example, an alkali metal hydroxide such as sodium hydroxide or potassium hydroxide. Hydroxide can also be present as a counter ion of the structure directing agent or by the use of aluminum hydroxide as a source of Al. Preferably the range $OH^-$:Si is greater than 0.05, and may, for example, be in the range of from 0.05 to 0.5. Optionally, the $OH^-$:Si ratio is less than 0.3.

The synthesis mixture optionally comprises seeds. The seeds may be any suitable zeolite seed crystals, such as ZSM-5, or ZSM-11 seed crystals. Preferably, the seeds are mesoporous ZSM-11 crystals. Preferably, the seed crystallite size is ≤100 nanometers. Such small crystallite size seeds are particularly advantageous for producing ZSM-11 crystallites with small crystallite sizes of this disclosure. The seeds may, for example, be present in an amount from about 0 to 20 wt %, in particular from about 0 to 10 wt %, preferably from about 0.01 to 10 wt % such as from about 0.1 wt % to about 5.0 wt % of the synthesis mixture. In a preferred embodiment, the synthesis mixture comprises seeds.

The present inventors have found that the synthesis of small crystal MEL framework type zeolite is favored by having a relatively high solids content in the synthesis mixture. Preferably, the $H_2O$:Si molar ratio is no more than 20, for example, in the range of from 5 to 20, preferably from 5 to 15, especially from 10 to 15.

The synthesis mixture may for example have a composition, expressed in terms of mole ratios, as indicated in the following TABLE A:

TABLE A

| Mole ratio | Preferred | More preferred | Especially preferred |
|---|---|---|---|
| Si:$Al_2$ | 15 to 70 | 15 to 40 | 20 to 30 |
| $OH^-$:Si | 0.05 to 0.5 | 0.05 to 0.3 | 0.05 to 0.2 |
| $M^+$:Si | 0.10 to 0.50 | 0.10 to 0.40 | 0.20 to 0.40 |
| SDA:Si | 0.005 to 0.20 | 0.01 to 0.1 | 0.02 to 0.08 |
| $H_2O$:Si | 5 to 20 | 5 to 15 | 10 to 15 |

Crystallization can be carried out under either static or stirred conditions in a suitable reactor vessel, such as for example, polypropylene jars or Teflon® lined or stainless steel autoclaves. Suitable crystallization conditions include a temperature of about 100° C. to about 200° C., such as about 135° C. to about 160° C. Preferably, the temperature is less than 150° C. The synthesis mixture may be held at the elevated temperature for a time sufficient for crystallization to occur at the temperature used, e.g., from about 1 day to about 100 days, optionally from 1 to 50 days for example about 2 days to about 40 days. The synthesis mixture may in some cases be maintained at a first temperature for a first period of from 1 hour to 10 days and then raised to a second, higher temperature for a period of from 1 hour to 40 days. After the crystallization step, the synthesized crystals are separated from the liquid, washed and then recovered.

Since the as-synthesized MEL framework type zeolite of this disclosure contains the structure directing agent within its pore structure, the product is usually activated before use in such a manner that the organic part of the structure directing agent, i.e. TBA, is at least partially removed from the zeolite.

The calcined MEL framework type zeolite of this disclosure is optionally prepared by calcining the MEL framework type zeolite of this disclosure to remove the structure directing agent. The MEL framework type zeolite may also be subjected to an ion-exchange step to replace the alkali or alkaline earth metal ions present in the as-synthesized product with other cations. Preferred replacing cations include metal ions, hydrogen ions, hydrogen precursor such as ammonium ions and mixtures thereof, more preferably hydrogen ions or hydrogen precursors. For instance the MEL framework type zeolite of this disclosure may be subjected to an ion-exchange step to replace the alkali or alkaline earth metal ions with ammonium cations, followed by calcination to convert the zeolite in ammonium form to a zeolite in hydrogen form. In one embodiment, the MEL framework type zeolite of this disclosure is first subjected to a calcination step, sometimes referred to as a "pre-calcination" to remove the structure directing agent from the pores of the MEL framework type zeolite, followed by an ion-exchange treatment, followed by a further calcination step.

The ion-exchange step may involve, for example, contacting the MEL framework type zeolite with an aqueous ion exchange solution. Such contact may be take place, for example, from 1 to 5 times. The contacting with the ion exchange solution is optionally at ambient temperature, or alternatively may be at an elevated temperature. For example, the zeolite of this disclosure may be ion exchanged by contact with aqueous ammonium nitrate solution at room temperature followed by drying and calcination.

Suitable calcination conditions include heating at a temperature of at least about 300° C., preferably at least about 400° C. for at least 1 minute and generally not longer than 20 hours, for example, for a period of from 1 hour to 12 hours. While subatmospheric pressure can be employed for the thermal treatment, atmospheric pressure is desired for reasons of convenience. For instance, the thermal treatment can be conducted at a temperature of from 400 to 600° C., for instance from 500 to 550° C., in the presence of an oxygen-containing gas.

The calcined MEL framework type zeolite of this disclosure typically has a chemical composition having the following molar relationship: $nSiO_2:Al_2O_3$, wherein n is at least 10, for example 10 to 60, more particularly 15 to 40, more preferably 20 to 40, more preferably 20 to 30.

The calcined MEL framework type zeolite of this disclosure may be used as is as a catalyst or as a sorbent without further treatment or it may be subjected to post-treatments such as steaming and/or acid washing.

Optionally, the calcined zeolite of this disclosure is subjected to steam treatment at a temperature of at least 200° C., preferably at least 350° C., more preferably at least 400° C., in some cases at least 500° C., for a period of from 1 to 20 hours, preferably from 2 to 10 hours. Optionally, the steamed zeolite is then subjected to treatment with an aqueous solution of an acid, preferably an organic acid, such as a carboxylic acid. Oxalic acid is a preferred acid. Optionally, the steamed zeolite is treated with an aqueous solution of an acid at a temperature of at least 50° C., preferably at least 60° C., for a period of at least 1 hour, preferably at least 4 hours, for example, in the range of from 5 to 20 hours.

Preferably, the post-treated MEL framework type zeolite has a chemical composition having the following molar relationship: $nSiO_2:Al_2O_3$, wherein n is at least 20, more preferably at least 50, and in some cases at least 100.

III. Catalyst Composition of the Third Aspect of this Disclosure Comprising the Novel MEL Zeolite Material of the First Aspect The MEL framework type zeolite of this disclosure can be used directly as a catalyst, or alternatively can be compounded with one or more other components such as binder and/or a second zeolite material. The MEL framework type zeolite may be used as an adsorbent or as a catalyst to catalyze a wide variety of organic compound conversion processes including many of present commercial/industrial importance. The conversion of hydrocarbon feeds can take place in any convenient mode, for example in fluidized bed, moving bed, or fixed bed reactors depending on the types of process desired.

A third aspect of this disclosure relates to catalyst compositions comprising a MEL framework type zeolite of the first aspect of this disclosure described above. The catalyst composition may be substantially free of any other component other than the MEL framework type zeolite. In such case, the MEL framework type zeolite is a self-supported catalyst composition.

The MEL framework type zeolite of this disclosure, when employed either as an adsorbent or as a catalyst in an organic compound conversion process in a catalyst composition should be preferably dehydrated, at least partially. This can be done by heating to a temperature in the range of about 100° C. to about 500° C., such as about 200° C. to about 370° C. in an atmosphere such as air, nitrogen, etc., and at atmospheric, subatmospheric or superatmospheric pressures for between 30 minutes and 48 hours. Dehydration can also be performed at room temperature merely by placing the MEL framework type zeolite in a vacuum, but a longer time is required to obtain a sufficient amount of dehydration.

The MEL framework type zeolite of this disclosure can be formulated into a catalyst composition by combination with other materials, such as hydrogenating components, binders and/or matrix materials that provide additional hardness or catalytic activity to the finished catalyst. These other materials can be inert or catalytically active materials. In particular, the MEL framework type zeolite of this disclosure may be combined with a second zeolite, such as zeolites having a 10- or 12-member ring structure in their crystallites. Non-limiting examples such second zeolite include: MWW framework type zeolites such as MCM-22, MCM-49, and MCM-56; MFI framework type zeolites such as ZSM-5; MOR framework zeolites such as mordenite; and the like; and mixtures and combinations thereof. The second zeolite may preferably has a constrain index in the range from 0.5 to 15. Where a second zeolite is included in the catalyst composition, it is preferred that the MEL framework type zeolite has a concentration in the catalyst composition of ≥50 wt %, e.g., ≥60 wt %, ≥70 wt %, ≥80 wt %, ≥90 wt %, ≥95 wt %, based on the total weight of the MEL framework type zeolite and the second zeolite.

The MEL framework type zeolite described herein may be intimately combined with a hydrogenating component, such as tungsten, vanadium, molybdenum, rhenium, nickel, cobalt, chromium, manganese, or a noble metal such as platinum or palladium where a hydrogenation-dehydrogenation function is to be performed. Such component can be incorporated in the composition by way of co-crystallization, exchanged into the composition to the extent a Group IIIA element, e.g., aluminum, is in the structure, impregnated therein or intimately physically admixed therewith. Such component can be impregnated in or onto the MEL framework type zeolite such as, for example, by, in the case of platinum, treating the MEL framework type zeolite with a solution containing a platinum metal-containing ion. Thus, suitable platinum compounds for this purpose include chloroplatinic acid, platinous chloride and various compounds containing the platinum amine complex. Combinations of metals and methods for their introduction can also be used.

As in the case of many catalysts, it may be desirable to incorporate the MEL framework type zeolite of this disclosure with another material resistant to the temperatures and other conditions employed in organic conversion processes. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the MEL framework type zeolite, i.e., combined therewith or present during synthesis of the MEL framework type zeolite, which is active, tends to change the conversion and/or selectivity of the catalyst in certain organic conversion processes. Inactive materials suitably serve as diluents to control the amount of conversion in a given process so that products can be obtained in an economic and orderly manner without employing other means for controlling the rate of reaction. These materials may be incorporated into naturally occurring clays, e.g., montmorillonite, bentonite, subbentonite and kaolin such as the kaolins commonly known as Dixie, McNamee, Georgia and Florida clays or others in which the main mineral constituent is halloysite, kaolinite, nacrite or anauxite, to improve the crush strength of the catalyst under commercial operating conditions. Such clays can be used in the raw state as originally mined or after being subjected to calcination, acid treatment or chemical modification. These binder materials are resistant to the temperatures and other conditions, e.g. mechanical attrition, which occur in various hydrocarbon conversion processes. Thus the MEL framework type zeolite of this disclosure or manufactured by the process of this disclosure may be used in the form of an extrudate with a binder. They are typically bound by forming a pill, sphere, or extrudate. The extrudate is usually formed by extruding the molecular sieve, optionally in the presence of a binder, and drying and calcining the resulting extrudate.

Use of a material in conjunction with the MEL framework type zeolite of this disclosure or manufactured by the process of this disclosure, i.e. combined therewith or present during synthesis of zeolite, tends to change the conversion and/or selectivity of the catalyst in certain organic conversion processes. Inactive materials suitably serve as diluents to control the amount of conversion in a given process so that products can be obtained in an economic and orderly manner without employing other means for controlling the rate of reaction. These materials may be incorporated into naturally occurring clays, e.g., bentonite and kaolin, to improve the crush strength of the catalyst under commercial operating conditions.

In addition to the foregoing materials, the MEL framework type zeolite of this disclosure can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of MEL framework type zeolite and inorganic oxide matrix may vary widely, with the MEL framework type zeolite content ranging from about 1 to about 100 percent by weight and more usually, particularly when the composite is prepared in the form of beads or extrudates, in the range of about 50 to about 80 weight percent of the composite.

Preferred binders in the catalyst composition are high surface area binders, such as high surface area alumina having a specific area of ≥200 $m^2/g$, even ≥250 $m^2/g$. Low surface area alumina having a specific area of ≤150 $m^2/g$ may work as well. Silica has been demonstrated as a useful binder in the catalyst composition.

In making the catalyst composition, the as-synthesized or calcined MEL framework type zeolite of the first aspect of this disclosure, in hydrogen-form, alkali form, or other form, can be mixed with other materials such as a binder, a second zeolite, and/or a hydrogenation metal, and other components such as water. The mixture can be formed into desired shape by, e.g., extrusion, molding, and the like. The thus formed catalyst composition can be optionally dried, calcined in nitrogen and/or air to obtain a catalyst composition. The catalyst composition can be further ion-exchanged with an ammonium salt solution, followed by drying and calcination to obtain a catalyst composition in hydrogen-form.

The catalyst composition of the second aspect of this disclosure can take any shape: cyclinder, solid sphere, trilobe, quadrulobe, eggshell sphere, and the like. The catalyst composition may be grounded into powder and used as such.

In the process of making the catalyst composition of the second aspect of this disclosure from the MEL framework type zeolite of the first aspect of this disclosure, some of the primary crystallites in the MEL framework type zeolite material may further agglomerize to form additional agglomerates or making existing agglomerates larger in size.

IV. Process for Converting Aromatics Hydrocarbons Using MEL Zeolite Material of the Fourth and Fifth Aspects of this Disclosure Certain MEL framework type zeolites are known. Examples of MEL framework type zeolites are ZSM-11 zeolites described in, e.g., U.S. Pat. Nos. 3,709,979; 3,804,746; 4,108,881; 4,941,963; 5,213,786; and 6,277,355. ZSM-11 were reported for use in catalytic dewaxing of in the production of hydrocarbon fuel products. See, e.g., Canadian Patent No. CA1281677C.

Using a MEL framework type zeolite in processes for converting aromatic hydrocarbons such as C8 aromatics hydrocarbons is per se novel. Thus, a fourth aspect of this disclosure relates to a process for converting a feed comprising C8 aromatic hydrocarbons, the process comprising: (I) feeding the aromatic hydrocarbon feed into a conversion reactor; and (II) contacting the C8 aromatic hydrocarbons at least partly in a liquid phase with a conversion catalyst composition comprising a MEL framework type zeolite in the conversion reactor under conversion conditions to effect isomerization of at least a portion of the C8 aromatic hydrocarbons to produce a conversion product effluent.

A high purity p-xylene product is typically produced by separating p-xylene from a p-xylene-rich aromatic hydrocarbon mixture comprising p-xylene, o-xylene, m-xylene, and optionally EB in a p-xylene separation/recovery system. The p-xylene recovery system can comprise, e.g., a crystallizer and/or an adsorption chromatography separating system known in the prior art. The p-xylene-depleted stream produced from the p-xylene recovery system (the “filtrate” from a crystallizer upon separation of the p-xylene crystals, or the “raffinate” from the adsorption chromatography separating system, collectively “raffinate” in this disclosure) is rich in m-xylene and o-xylene, and contains p-xylene at a concentration typically below its concentration in an equilibrium mixture consisting of m-xylene, o-xylene, and p-xylene. To increase yield of p-xylene, the raffinate stream may be fed into an isomerization unit, where the xylenes undergo isomerization reactions in contacting an isomerization catalyst system to produce an isomerized effluent rich in p-xylene compared to the raffinate. At least a portion of the isomerized effluent, after optional separation and removal of lighter hydrocarbons that may be produced in the isomerization unit, can be recycled to the p-xylene recovery system, forming a “xylenes loop.”

Xylenes isomerization can be carried out under conditions where the C8 aromatic hydrocarbons are substantially in vapor phase in the presence of an isomerization catalyst (vapor-phase isomerization, or “VPI”).

Newer generation technology have been developed to allow xylenes isomerization at significantly lower temperature in the presence of an isomerization catalyst, where the C8 aromatic hydrocarbons are substantially in liquid phase (liquid-phase isomerization, or “LPI”). The use of LPI vs. traditional VPI can reduce the number of phase changes (liquid to/from vapor) required to process the C8 aromatic feed. This provides the process with sustainability advantages in the form of significant energy savings. It would be highly advantageous for any p-xylene production plant to deploy a LPI unit, in addition to or in lieu of a VPI unit. For existing p-xylene production facilities lacking a LPI, it would be highly advantageous to add a LPI unit to compliment the VPI unit or replace the VPI unit.

Exemplary LPI processes and catalyst systems useful therefor are described in U.S. Patent Application Publication Nos. 2011/0263918 and 2011/0319688, 2017/0297977, 2016/0257631, and U.S. Pat. No. 9,890,094, the contents of all of which are incorporated herein by reference in their entirety. In the LPI processes described in these references, typically a MFI framework type zeolite (e.g., ZSM-5) is used as the catalyst.

We have surprisingly found that ZSM-11 zeolite can be used in LPI of C8 aromatic hydrocarbons, resulting in significantly lower xylenes loss compared to a process using ZSM-5 zeolite as the catalyst at WHSV of conventional LPI processes, such as at 2.5 and 5 $hour^{-1}$.

Even more surprisingly, we have found that, by using the novel ZSM-11 zeolite of this disclosure having small crystallite size and/or a low $SiO_2/Al_2O_3$ ratio, a LPI process can achieve an extraordinarily high p-xylene selectivity at a large range of WHSV, making it advantageous to operate an LPI process at not only conventional WHSV such as 2.5 and 5.0 $hour^{-1}$, but also at high WHSV>5 $hour^{-1}$, such as ≥10 $hour^{-1}$, or ≥15 $hour^{-1}$, and up to 20 $hour^{-1}$. Such high throughput LPI processes, conventionally infeasible using a MFI framework type zeolite such as ZSM-5, now made possible by the novel MEL framework type zeolite of this disclosure, can be particularly attractive.

Any MEL framework type zeolite may be included in the conversion catalyst composition. Preferably the MEL framework type zeolite is at least partly in hydrogen-form. Preferably the MEL framework zeolite is calcined.

The MEL framework zeolite included in the conversion catalyst composition in the aromatic hydrocarbon conversion processes of this disclosure can advantageously have a $SiO_2/Al_2O_3$ molar ratio from 10 to 60, preferably from 15 to 50, preferably from 15 to 40, preferably from 20 to 40, such as from 20 to 30. The lower this ratio, the more active the zeolite tends to be in catalyzing the conversion of aromatic hydrocarbons.

The MEL framework zeolite included in the conversion catalyst composition can advantageously comprise a plurality of small crystallites, such as those having crystallite sizes as determined by TEM imaging analysis ≤200 nm, preferably ≤150 nm, preferably ≤100 nm, preferably ≤80 nm, preferably ≤70 nm, preferably ≤60 nm, preferably ≤50 nm, such as ≤30 nm. At such small crystallite sizes, the zeolite is particularly effective and efficient in catalyzing the conversion of aromatic hydrocarbons, especially the isomerization of the xylenes.

The crystallites forming the MEL framework zeolite included in the conversion catalyst composition can comprise, based on the total number of crystallites, ≥75%, such as ≥80%, ≥85%, ≥90%, ≥95%, up to 98% of the crystallites having crystallite sizes as determined by TEM imaging analysis ≤200 nm, preferably ≤150 nm, preferably ≤100 nm, preferably ≤80 nm, preferably ≤70 nm, preferably ≤60 nm, preferably ≤50 nm, preferably ≤50 nm, such as ≤30 nm.

The crystallites forming the MEL framework type zeolite included in the conversion catalyst composition can form a number of agglomerates with irregular shapes.

The MEL framework zeolite included in the conversion catalyst composition can advantageously have BET total surface area of A(st) that can vary from a1 to a2 $m^2/g$, where a1 and a2 can be, independently, e.g., 300, 320, 340, 350, 360, 380, 400, 420, 440, 450, 460, 480, 500, 520, 540, 550, 560, 580, 600, as long as a1<a2. In certain embodiments it is preferred that a1=400 and a2=500. In certain embodiments it is preferred that a1=400 and a2=475.

The MEL framework zeolite included in the conversion catalyst composition can advantagedly have a mesopore surface area of A(mp) that is ≥15% (e.g., ≥16%, ≥18%, ≥20%, ≥22%, ≥24%, ≥25%) of the total surface area A(st) discussed above. In certain embodiments it is preferred that A(mp)≥20%*A(st). In certain embodiments, it is preferred that A(mp)≤40%*A(st). In certain embodiments, it is preferred that A(mp)≤30%*A(st). The high mesopore area A(mp) of the zeolite material of this disclosure is another reason why it exhibits a high catalytic activity when used as a catalyst, such as a catalyst for converting aromatic hydrocarbons.

The conversion catalyst composition can comprise, in addition to a MEL framework type zeolite, a binder such as alumina, silica, zirconia, zircon, chromia, kaolin, and other refractory materials, and mixtures and combinations thereof. Binders with high surface area such as high surface area silica, high surface area silica, are preferred.

The conversion catalyst composition can comprise, in addition to a MEL framework type zeolite, a second zeolite such as a zeolite of the MFI framework type (e.g., ZSM-5), a zeolite of the MWW framework type (e.g., MCM-22, MCM-49, and the like), and mixtures and combinations thereof. When the second zeolite is included, it is preferred that the MEL framework type zeolite is included at a concentration of ≥50 wt %, e.g., ≥60 wt %, ≥70 wt %, ≥80 wt %, ≥90 wt %, or even ≥95 wt %, based on the total weight of the MEL framework type zeolite and the second zeolite. Such second zeolite preferably has a 10- or 12-member ring the crystallite structures thereof. Such second zeolite preferably has a constraint index in the range from 0.5 to 15, preferably from 1 to 10.

Particularly advantageous MEL framework zeolites that can be included in the conversion catalyst composition used in the aromatic hydrocarbon conversion processes of this disclosure are those of the first aspect of this disclosure, as described in detail above.

On contacting the C8 aromatic hydrocarbons, especially the xylene molecules, the xylene molecules can undergo isomerization reactions. Typically, the aromatic hydrocarbon feed comprises p-xylene, o-xylene, m-xylene, and EB. The aromatic hydrocarbon feed can be a portion of a raffinate from a p-xylene separation/recovery system.

The aromatic feed can be derived from, e.g., an effluent from a C8 aromatic hydrocarbon distillation column, a p-xylene depleted raffinate stream produced from a p-xylene separation/recovery system comprising an adsorption chromatography system, or a p-xylene depleted filtrate stream produced from a p-xylene separation/recovery system comprising a p-xylene crystallizer, or a mixture thereof. In this disclosure, the raffinate stream and the filtrate stream are collectively called a raffinate stream below.

In certain embodiments the aromatic hydrocarbon feed can comprise p-xylene at various concentration of C(pX) ranging from c1 to c2 wt %, based on the total weight of the C8 aromatics present in the aromatic hydrocarbon feed, wherein c1 and c2 can be, independently, e.g., 0.5, 1, 2, 3, 4, 5, 6, 7, 8, 9, 10, 11, 12, 13, 14, 15, 16, 17, 18, 19, 20, as long as c1<c2. Typically C(pX) is lower than the p-xylene concentration in an equilibrium mixture consisting of p-xylene, m-xylene, and o-xylene at the same temperature. Preferably C(pX)≤15. More preferably C(pX)≤10. Still more preferably C(pX)≤8.

In certain embodiments the aromatic hydrocarbon feed can comprise m-xylene at various concentration of C(mX) ranging from m1 to m2 wt %, based on the total weight of the C8 aromatics present in the aromatic hydrocarbon feed, wherein m1 and m2 can be, independently, e.g., 20, 25, 30, 35, 40, 45, 50, 55, 60, 65, 70, 75, or 80, as long as m1<m2. C(mX) can be significantly higher than the m-xylene concentration in an equilibrium mixture consisting of p-xylene, m-xylene, and o-xylene at the same temperature, especially if the aromatic hydrocarbon feed consists essentially of xylenes only and is substantially free of EB.

In certain embodiments the aromatic hydrocarbon feed can comprise o-xylene at various concentration of C(oX) ranging from n1 to n2 wt %, based on the total weight of the C8 aromatics present in the aromatic hydrocarbon feed, wherein n1 and n2 can be, independently, e.g., 10, 15, 20, 25, 30, 35, 40, 45, 50, as long as n1<n2. C(oX) can be significantly higher than the o-xylene concentration in an equilibrium mixture consisting of p-xylene, m-xylene, and o-xylene at the same temperature, especially if the aromatic hydrocarbon feed consists essentially of xylenes only and is substantially free of EB.

Among all xylenes present in the aromatic hydrocarbon feed, m-xylene and o-xylene can be present at any ratio. Thus, the ratio of m-xylene to o-xylene can range from r1 to r2, where r1 and r2 can be, independently, e.g., 0.1, 0.2, 0.3, 0.4, 0.5, 0.6, 0.7, 0.8, 0.9, 1, 2, 3, 4, 5, 6, 7, 8, 9, 10, as long as r1<r2.

In certain embodiments the aromatic hydrocarbon feed fed to the conversion reactor can comprise xylenes in total at a concentration of C(aX) wt % ranging from c3 to c4 wt %, based on the total weight of the aromatic hydrocarbon feed, wherein c3 and c4 can be, independently, e.g., 50, 55, 60, 65, 70, 75, 80, 85, 90, 91, 92, 93, 94, 95, 96, 97, 98, or 99, as long as c3<c4. The aromatic hydrocarbon feed can consist essentially of xylenes and EB.

In certain embodiments the aromatic hydrocarbon feed can comprise EB at a concentration of C(EB) wt % ranging from c5 to c6 wt %, based on the total weight of the aromatic hydrocarbon feed, wherein c5 and c6 can be, independently, e.g., 1, 2, 3, 4, 5, 6, 7, 8, 9, 10, 12, 14, 15, 16, 18, 20, 22, 24, 25, 26, 28, 30, as long as c5<c6. Preferably 2≤C(EB)≤25. More preferably 3≤C(EB)≤20. Still more preferably 5≤C(EB)≤15.

In certain embodiments the aromatic hydrocarbon feed comprise C8 aromatic hydrocarbons (i.e., the xylenes and EB) at an aggregate concentration of, e.g., ≥90, or ≥92, or ≥94, or ≥95, or ≥96, or ≥98, or even ≥99 wt %, based on the total weight of the aromatic hydrocarbon feed.

In certain embodiments the aromatic hydrocarbon feed can comprise C9+ aromatic hydrocarbons at a concentration of C(C9+A) wt % ranging from c7 to c8 wt %, based on the total weight of the aromatic hydrocarbon feed, wherein c7 and c8 can be, independently, e.g., 1, 20, 40, 50, 60, 80, 100, 200, 400, 500, 600, 800, 1000, as long as c7<c8.

The aromatic hydrocarbon feed, depending on its source (e.g., a xylenes distillation column, a p-xylene crystallier, or an adsorption chromatography separation system), may comprise toluene at various amounts, but typically no greater than 1 wt %, based on the total weight of the aromatic hydrocarbon feed.

The aromatic hydrocarbon feed, depending on its source, may comprise C7− aromatic hydrocarbons (toluene and benzene in total) at various amounts, e.g., ranging from c9 to c10 wppm by weight, based on the total weight of the aromatic hydrocarbon feed, where c9 and c10 can be, independently, e.g., 10, 20, 40, 50, 60, 80, 100, 200, 400, 500, 600, 800, 1000, 2000, 4000, 5000, 6000, 8000, 10000, 20000, as long as c9<c10.

Exemplary conversion conditions in the aromatic hydrocarbon conversion processes of this disclosure can include a temperature in the range from t1 to t2° C., where t1 and t2 can be, independently, e.g., 100, 120, 140, 150, 160, 180, 200, 220, 240, 250, 260, 280, 300, 320, 340, 350, as long as t1<t2. Preferably t1=150 and t2=300. Preferably t1=180 and t2=300. Preferably t1=200 and t2=280. Preferably t1=220 and t2=260. Preferably t1=240 and t2=260. The low operating temperature of the processes can result in significant energy savings compared to a conventional VPI process which typically runs at a significantly higher temperature.

Exemplary conversion conditions in the aromatic hydrocarbon conversion processes of this disclosure can include a WHSV based on the flow rate of the aromatic hydrocarbon feed and the weight of the conversion catalyst composition, in a range from w1 to w2 hour$^{-1}$, where w1 and w2 can be, independently, e.g., 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.0, 9.5, 10, 11, 12, 13, 14, 15, 16, 17, 18, 19, 20, as long as w1<w2. Preferably w1=1.0 and w2=20. Preferably w1=2.0 and w2=20. Preferably w1=5.0 and w2=20. Preferably w1=8.0 and w2=10. Preferably w1=5.0 and w2=15. Preferably w1=10 and w2=15. Such high throughput processes where w1>5.0, e.g., w1≥8.0, w1≥10, w1≥15, can be particularly advantageous. As described above and demonstrated in the examples below, by using certain MEL framework type zeolite of the first aspect in this disclosure, high p-xylene selectivity not feasible in conventional processes using a ZSM-5-based catalyst at such high WHSV can be achieved.

Exemplary conversion conditions in the aromatic hydrocarbon conversion processes of this disclosure typically includes an internal pressure in the conversion reactor sufficient to maintain a great majority, e.g., ≥80 mol %, such as ≥85 mol %, ≥90 mol %, ≥95 mol %, ≥98 mol %, or even substantially all of the C8 aromatic hydrocarbons in the aromatic hydrocarbon feed in liquid phase at the given temperature in the conversion reactor. For example, for a LPI reaction temperature at 240° C., the pressure is typically ≥1830 kPa.

Exemplary conversion conditions in the aromatic hydrocarbon conversion process of this disclosure can include feeding molecular hydrogen into the conversion reactor. Any suitable quantity of molecular hydrogen may be supplied into the conversion reactor. Exemplary quantity of molecular hydrogen supplied to the conversion reactor can be in a range from h1 to h2 wppm, based on the total weight of the aromatic hydrocarbon feed, where h1 and h2 can be, e.g., 1, 2, 4, 5, 6, 8, 10, 20, 40, 50, 60, 80, 100, 200, 400, 500, 600, 800, or 1000, as long as h1<h2. Preferably h1=4 and h2=250. Where molecular hydrogen is supplied to the conversion reactor, it is highly desirable that the pressure in the conversion reactor is maintained sufficient to dissolve a great majority, e.g., ≥80%, ≥85%, ≥90%, ≥95%, ≥98%, or even substantially all, of the molecular hydrogen in the aromatic hydrocarbon feed, such that the conversion reactions in the conversion reactor substantially in liquid phase. Without intending to be bound by a particular theory, it is believed that co-feeding a quantity of molecular hydrogen into the conversion reactor may inhibit coke formation on the conversion catalyst composition, thereby extending the life of the conversion catalyst composition.

Surprisingly, we have found that a conversion catalyst composition comprising a MEL framework type zeolite, especially a MEL framework type zeolite of the first aspect of this disclosure, demonstrated much lower deactivation rate compared to a MFI zeolite-based, such as ZSM-5-based, catalyst composition in LPI processes in the absence of co-feeding hydrogen into the LPI reactor. While it would be desirable to co-feed molecular hydrogen to a LPI conversion process utilizing a MFI zeolite-based catalyst composition to extend the service life of the catalyst composition, it is not necessary to do so in a process of this disclosure using a MEL framework type zeolite-based conversion catalyst composition due to its exceedingly low deactivation rate even in the absence of co-fed molecular hydrogen. Thus, in a particularly advantageous embodiment of the aromatic hydrocarbon conversion processes of this disclosure, molecular hydrogen is not co-fed into the conversion reactor. Such elimination of hydrogen co-feeding, hence the elimination of hydrogen consumption, hydrogen supply lines, hydrogen compressor, and hydrogen recycle lines from the conversion reactor, substantially simplifies the process and system design, resulting in lower costs for system equipment, and simpler and more reliable operation of the conversion process and the conversion reactor.

Xylenes loss in an aromatic hydrocarbon conversion process of this disclosure ("Lx(1)") can be calculated as $Lx(1)=100\%*(W1-W2)/W1$, where W1 is the aggregate weight of all xylenes present in the aromatic hydrocarbon feed, and W2 is the aggregate weight of all xylenes present in the conversion product effluent. In certain embodiments of aromatic hydrocarbon conversion processes of this disclosure, the xylenes loss can reach a level of ≤0.2 wt %, e.g., ≤0.15 wt %, ≤0.10 wt %, and even ≤0.05 wt %, at a WHSV of 2.5 $hour^{-1}$, which is significantly lower than a comparative process using a ZSM-5-based catalyst composition, as demonstrated in the Examples below.

The conversion product effluent from the conversion reactor can advantageously comprise p-xylene at a concentration higher than the aromatic hydrocarbon feed, thanks to the isomerization reactions resulting in the conversion and m-xylene and/or o-xylene to p-xylene. The conversion product effluent can further comprises C9+ aromatics and C7− aromatics, which can be supplied into the conversion reactor as impurities in the aromatic hydrocarbon feed or produced from side reactions in the conversion reactor. The production of additional C9+ aromatic hydrocarbons and C7− aromatic hydrocarbons are often associated with xylenes loss, and hence are not desirable.

In certain embodiments of the aromatic hydrocarbon conversion processes of this disclosure, the processes have a WHSV of at least 2.5 $hour^{-1}$, and exhibit a C9+ aromatic hydrocarbons yield of at most 3000 ppm by weight, such as at most 1600 ppm, or at most 1000 ppm, based on the total weight of the conversion product effluent. Such C9+ aromatic hydrocarbon yield achievable by using a MEL framework type zeolite in the conversion catalyst composition, especially at low WHSV of 2.5 $hour^{-1}$, is significantly lower than demonstrated in a comparative process using a ZSM-5-based zeolite in the catalyst composition.

In certain embodiments of the aromatic hydrocarbon conversion processes of this disclosure, the processes have a WHSV of at least 5.0 $hour^{-1}$, and exhibit a C9+ aromatic hydrocarbons yield of at most 1000 ppm by weight, such as at most 800 ppm, or at most 600 ppm, or at most 500 ppm, based on the total weight of the conversion product effluent. Such C9+ aromatic hydrocarbon yield achievable by using a MEL framework type zeolite in the conversion catalyst composition, especially at low WHSV of 5.0 $hour^{-1}$, is significantly lower than demonstrated in a comparative process using a ZSM-5-based zeolite in the catalyst composition.

In certain other embodiments of the aromatic hydrocarbon conversion processes of this disclosure, the processes have a WHSV of at least 10 $hour^{-1}$, and exhibit a C9+ aromatic hydrocarbons yield of at most 1000 ppm by weight, such as at most 800 ppm, or at most 700 ppm, or at most 600 ppm, or at most 500 ppm, based on the total weight of the conversion product effluent.

In certain other embodiments of the aromatic hydrocarbon conversion processes of this disclosure, the processes have a WHSV of at least 2.5 $hour^{-1}$, and exhibit a benzene yield of at most 1000 ppm by weight, such as at most 800 ppm, or at most 700 ppm, or at most 600 ppm, or at most 500 ppm, based on the total weight of the conversion product effluent.

In certain other embodiments of the aromatic hydrocarbon conversion processes of this disclosure, the processes have a WHSV of at least 5.0 $hour^{-1}$, and exhibit a benzene yield of at most 800 ppm, such as at most 700 ppm, or at most 600 ppm, or at most 500 ppm, based on the total weight of the conversion product effluent.

In certain other embodiments of the aromatic hydrocarbon conversion processes of this disclosure, the processes have a WHSV of at least 10 $hour^{-1}$, and exhibit a benzene yield of at most 500 ppm, such as at most 400 ppm, or at most 300 ppm.

In certain other embodiments of the aromatic hydrocarbon conversion processes of this disclosure, the processes have a WHSV of at least 2.5 $hour^{-1}$, and exhibit a toluene yield of at most 800 ppm, such as at most 600 ppm, at most 500 ppm, or at most 300 ppm.

In certain other embodiments of the aromatic hydrocarbon conversion processes of this disclosure, the processes have a WHSV of at least 5.0 $hour^{-1}$, and exhibit a toluene yield of at most 200 ppm, such as at most 100 ppm, or at most 50 ppm.

In certain other embodiments of the aromatic hydrocarbon conversion processes of this disclosure, the processes have a WHSV of at least 10 $hour^{-1}$, and exhibit a toluene yield of at most 200 ppm, such as at most 100 ppm, or at most 50 ppm.

As discussed above, an advantage of the aromatic hydrocarbon conversion processes of this disclosure using a conversion catalyst composition comprising a MEL framework type zeolite is high p-xylene selectivity in the conversion product effluent produced from the conversion reactor, and in certain embodiments even at high WHSV>5 $hour^{-1}$, such as ≥10 $hour^{-1}$ and even ≥15 $hour^{-1}$. In this disclosure, "p-xylene selectivity" is defined as the p-xylene concentration among all xylenes in the conversion product effluent. Thus, in certain embodiments, the aromatic hydrocarbon conversion processes of this disclosure exhibit a p-xylene selectivity of ≥20%, or ≥21%, or ≥22%, or ≥23%, at WHSV of 2.5 $hour^{-1}$ when the aromatic hydrocarbon feed comprises p-xylene at a concentration of ≤15 wt % (preferably ≤10 wt %, preferably ≤8 wt %, preferably ≤6 wt %, preferably ≤5 wt %, preferably ≤3 wt %, preferably ≤2 wt %) based on the total weight of the xylenes in the aromatic hydrocarbon feed. In certain embodiments, the aromatic hydrocarbon conversion processes of this disclosure even exhibit a p-xylene selectivity of ≥20%, or ≥21%, or ≥22%, or ≥23%, at WHSV of 5.0 $hour^{-1}$ when the aromatic hydrocarbon feed comprises p-xylene at a concentration of ≤15 wt % (preferably ≤10 wt %, preferably ≤8 wt %, preferably ≤6 wt %, preferably ≤5 wt %, preferably ≤3 wt %, preferably ≤2 wt %). In certain embodiments, the aromatic hydrocarbon conversion processes of this disclosure exhibit a p-xylene selectivity of ≥20%, or ≥21%, or ≥22%, or ≥23%, at WHSV of 10 $hour^{-1}$ when the aromatic hydrocarbon feed comprises p-xylene at a concentration of ≤15 wt % (preferably ≤10 wt %, preferably ≤8 wt %, preferably ≤6 wt %, preferably ≤5 wt %, preferably ≤3 wt %, preferably ≤2 wt %). In certain embodiments, the aromatic hydrocarbon conversion processes of this disclosure may even exhibit a p-xylene selectivity of ≥20%, or ≥21%, or ≥22%, or ≥23%, at WHSV of 15 $hour^{-1}$ when the aromatic hydrocarbon feed comprises p-xylene at a concentration of ≤15 wt % (preferably ≤10 wt %, preferably ≤8 wt %, preferably ≤6 wt %, preferably ≤5 wt %, preferably ≤3 wt %, preferably ≤2 wt %). Such high p-xylene selectivity at high WHSV is not achievable in a comparative process using a ZSM-5-based catalyst composition, and is particularly advantageous. The fact that a conversion process of this disclosure using a MEL framework zeolite in the catalyst composition can achieve such high p-xylene selectivity at high WHSV is totally unexpected and very surprising.

The aromatic hydrocarbon conversion processes of this disclosure may be characterized a LPI process using a catalyst composition comprising a MEL framework type zeolite. The conversion reactor may be called a LPI reactor or LPI unit.

The LPI process is more energy efficient than a VPI process. A VPI process, on the other hand, can be more effective in converting ethylbenzene than a LPI process. Thus, if an aromatic hydrocarbon feed subject to isomerization conversion comprises ethylbenzene at an appreciable concentration, it may accumulate in a xylenes loop including only a LPI unit without a VPI reactor (or VPI unit) unless a portion of the feed is purged. Purging of the feed or ethylbenzene accumulation in the xylenes loop are both undesirable. As such, it may be desired to maintain both a LPI unit and a VPI unit in an aromatics production complex. In such case, the LPI and the VPI units may be fed with the aromatic hydrocarbon feeds with the same or different compositions with various quantities. In one embodiment, the LPI unit and the VPI unit are arranged in parallel so that they may receive aromatic feed from a common source with substantially the same composition. In another embodiment, the LPI unit and the VPI unit may operate in series, such that an aromatic hydrocarbon feed is first fed into a LPI unit to accomplish at least a partial isomerization of the xylenes to produce a LPI effluent which, in turn, is fed into the VPI unit, where additional xylenes isomerization and ethylbenzene conversion occur. Alternatively, the VPI unit may be the lead unit receiving an aromatic hydrocarbon feed and produce an ethylbenzene-depleted VPI effluent which, in turn, is fed into a LPI unit to further xylene isomerization reactions.

This disclosure is further illustrated by the following non-limiting examples. Numerous modifications and variations are possible and it is to be understood that within the scope of the appended claims, this disclosure may be practiced otherwise than as specifically described herein.

This disclosure is further illustrated by the following non-limiting examples.

EXAMPLES

In the following Examples, "TBABr" stands for tetrabutylammonium bromide (a templating agent), "XRD" for X-ray diffraction, "SEM" for scanning electron microscopy, "TEM" for transmission electron microscopy, "DI water" for deionized water, "HSA" for high surface area (i.e., having a specific surface area ≥200 $m^2/g$), "LSA" for low surface area (i.e., having a specific surface area ≤150 $m^2/g$); all parts are by weight unless otherwise indicated.

Measurement of Crystallite Size

The measurement of crystallite (i.e., primary particle) size was carried out as follows. Several TEM photographs of the zeolite sample were taken, primary particles were identified and measured. For each primary particle having an aspect ratio greater than 1, the longest dimension was identified by drawing a line between the two points at the edge of the particle which were the furthest apart. Then the length of the primary particle along a 45° diagonal to that longest dimension and passing through the mid-point of that longest dimension was measured as the particle size.

Measurement of Total Surface Area and Mesopore Surface Area by BET

The total BET and the t-Plot micropore surface area were measured by nitrogen adsorption/desorption after degassing of the calcined zeolite powders for 4 hours at 350° C. The mesopore surface area (i.e., the external surface area) was obtained by the subtraction of the t-plot micropore from the total BET surface area. More information regarding the method can be found, for example, in "*Characterization of Porous Solids and Powders: Surface Area, Pore Size and Density*", S. Lowell et Springer, 2004.

Alpha Value

The alpha value is a measure of the cracking activity of a catalyst and is described in U.S. Pat. No. 3,354,078 and in the Journal of Catalysis, Vol. 4, p. 527 (1965); Vol. 6, p. 278 (1966) and Vol. 61, p. 395 (1980), each incorporated herein by reference. The experimental conditions of the test used herein included a constant temperature of 538° C. and a variable flow rate as described in detail in the Journal of Catalysis, Vol. 61, p. 395 (1980).

Example A1: Synthesis of a First ZSM-11 Zeolite Having a $SiO_2/Al_2O_3$ Molar Ratio of ~50

A first ZSM-11 zeolite material with $SiO_2/Al_2O_3$ molar ratio of 50 was synthesized from a synthesis mixture comprising TBABr aqueous solution, Ultrasil™ precipitation silica, aluminum sulfate sol, NaOH aqueous solution, and ZSM-11 seeds. The synthesis mixture had the following molar composition:

$SiO_2/Al_2O_3$ ~55
$H_2O/SiO_2$ ~14.2
$OH^-/SiO_2$ ~0.14
$Na^+/SiO_2$ ~0.25
$TBABr/SiO_2$ ~0.05

Figure 2:
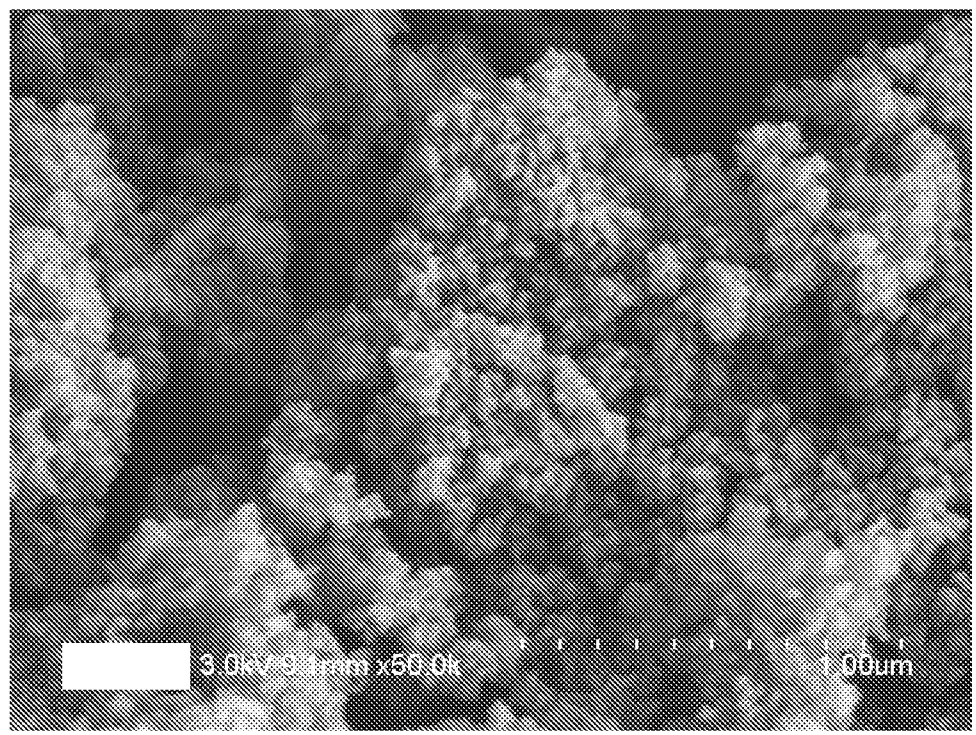
Figure 3:
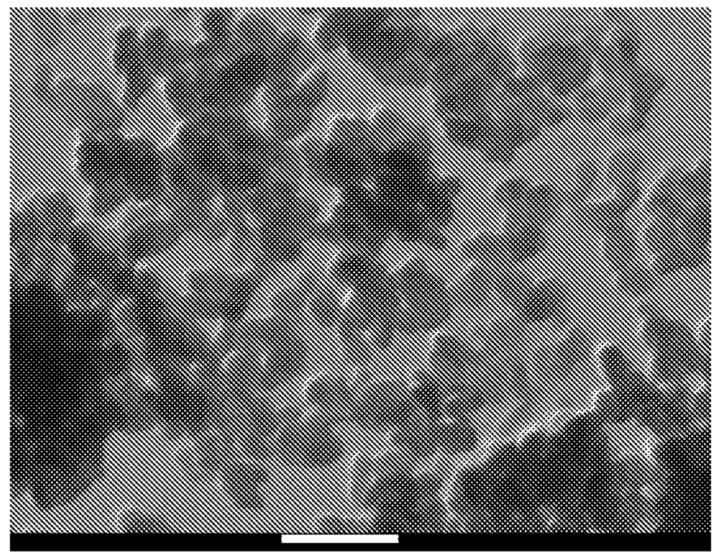

The mixture was reacted at 280° F. (138° C.) in an autoclave with stirring for 72 hours. The product was filtered, washed with DI water and dried at 250° F. (120° C.). The XRD diagram of the resulting crystals in FIG. 1 shows the typical pattern of a ZSM-11 zeolite. A SEM image of the resulting crystals, shown in FIG. 2, indicates irregular-shaped agglomerates formed from crystallites, where the crystallites have sizes <50 nanometers. A TEM image of the resulting crystals, shown in FIG. 3, indicates a majority of the crystallites (primary particles) have sizes ≤400 angstrom and aspect rations ≤2. The resulting crystals exhibited a silica/alumina molar ratio of ~50. A portion of the as-synthesized zeolite crystals were converted into the hydrogen form by three ion exchanges with ammonium nitrate solution at room temperature, followed by drying at 250° F. (120° C.) and calcination at 1000° F. (540° C.) for 6 hours. The hydrogen-form zeolite was measured to have an alpha value of 800, a hexane adsorption value of 98 mg/g, a total surface area of 490 $m^2/g$ and an external surface area of 134 $m^2/g$.

Example A2: Synthesis of a Second ZSM-11 Zeolite Having a $SiO_2/Al_2O_3$ Molar Ratio of ~25

A second ZSM-11 zeolite material with $SiO_2/Al_2O_3$ molar ratio of 24.7 was synthesized from a synthesis mixture comprising TBABr aqueous solution, Ultrasil™ precipitation silica, aluminum sulfate sol, NaOH aqueous solution, and ZSM-11 seeds. The synthesis mixture had the following molar composition:

$SiO_2/Al_2O_3$ ~26
$H_2O/SiO_2$ ~14.3
$OH^-/SiO_2$ ~0.1
$Na^+/SiO_2$ ~0.37
$TBABr/SiO_2$ ~0.05

Figure 6:
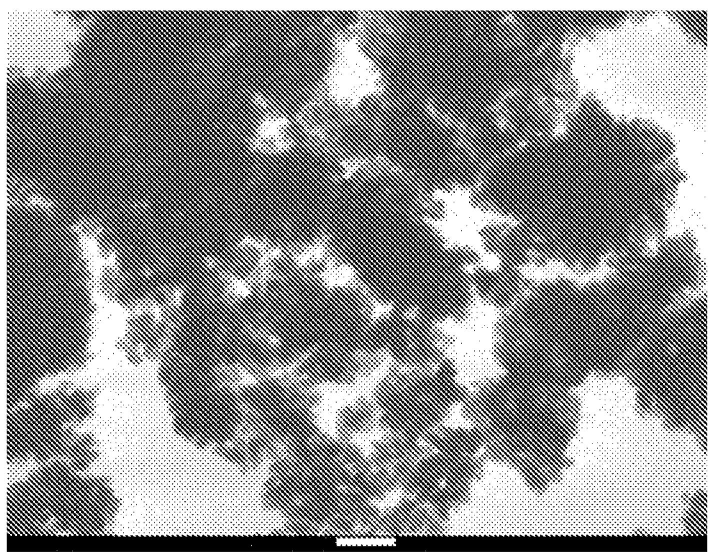
FIGS. 4, 5, and 6 are XRD graph, a SEM image, and a TEM image of a ZSM-11 zeolite synthesized in Example A2 of this disclosure, respectively.
Figure 4:
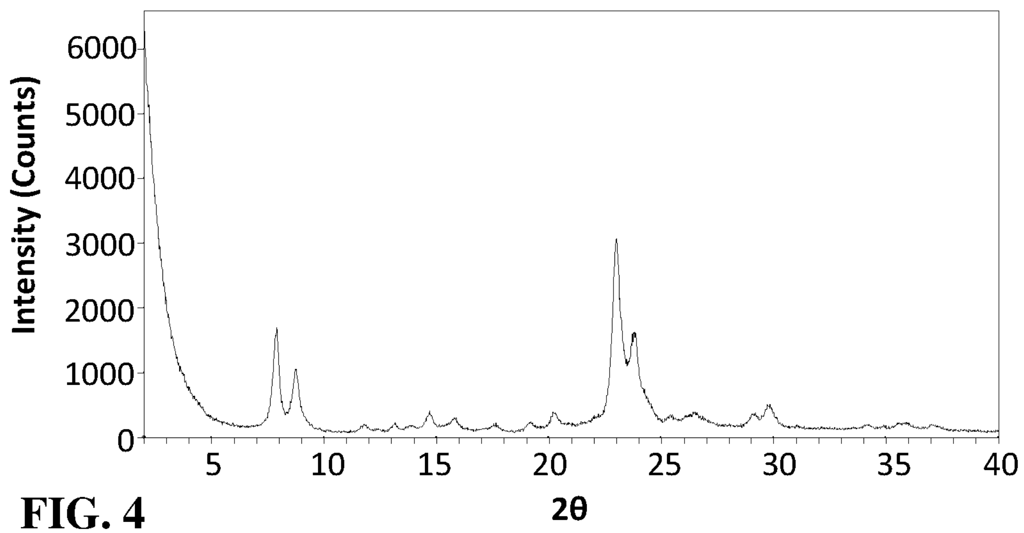
Figure 5:
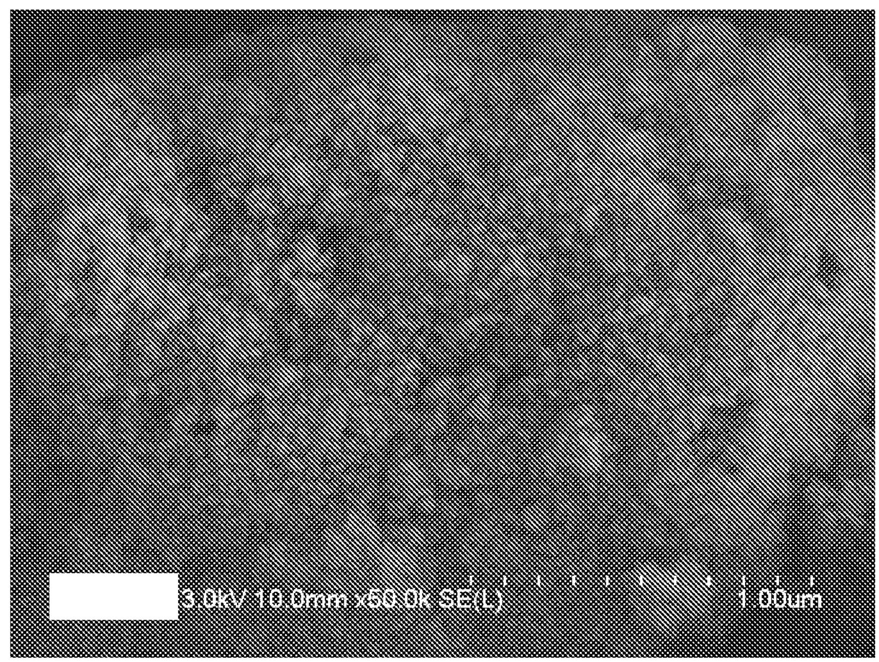

The mixture was reacted at 280° F. (138° C.) in an autoclave with stirring for 72 hours. The product was filtered, washed with DI water and dried at 250° F. (120° C.). The XRD graph in FIG. 4 of the resulting crystals shows the typical pattern of a ZSM-11 zeolite. A SEM image of the resulting crystals, shown in FIG. 5, indicates irregular-shaped agglomerates formed from crystallites, where the crystallites have sizes <50 nanometers. A TEM image of the resulting crystals, shown in FIG. 6, indicates a majority of the crystallites (primary particles) have sizes ≤400 angstrom and aspect ratios ≤2. The resulting crystals exhibited a silica/alumina molar ratio of 24.7. A portion of the as-synthesized zeolite crystals were converted into the hydrogen form by three ion exchanges with ammonium nitrate solution at room temperature, followed by drying at 250° F. (120° C.) and calcination at 1000° F. (540° C.) for 6 hours. The hydrogen-form zeolite was measured to have an alpha value of 1300, a hexane adsorption value of 100 mg/g, a total surface area of 461 $m^2/g$ and an external surface area of 158 $m^2/g$.

Example A3: Synthesis of a Third ZSM-11 Zeolite Having a $SiO_2/Al_2O_3$ Ratio of ~28

A third ZSM-11 zeolite material with $SiO_2/Al_2O_3$ molar ratio of 28 was synthesized from a synthesis mixture comprising TBABr aqueous solution, Ultrasil™ precipitation silica, aluminum sulfate sol, NaOH aqueous solution, and ZSM-11 seeds. The synthesis mixture had the following molar composition:

$SiO_2/Al_2O_3$ ~29
$H_2O/SiO_2$ ~13.6
$OH^-/SiO_2$ ~0.1
$Na^+/SiO_2$ ~0.31
$TBABr/SiO_2$ ~0.08

Figure 7:
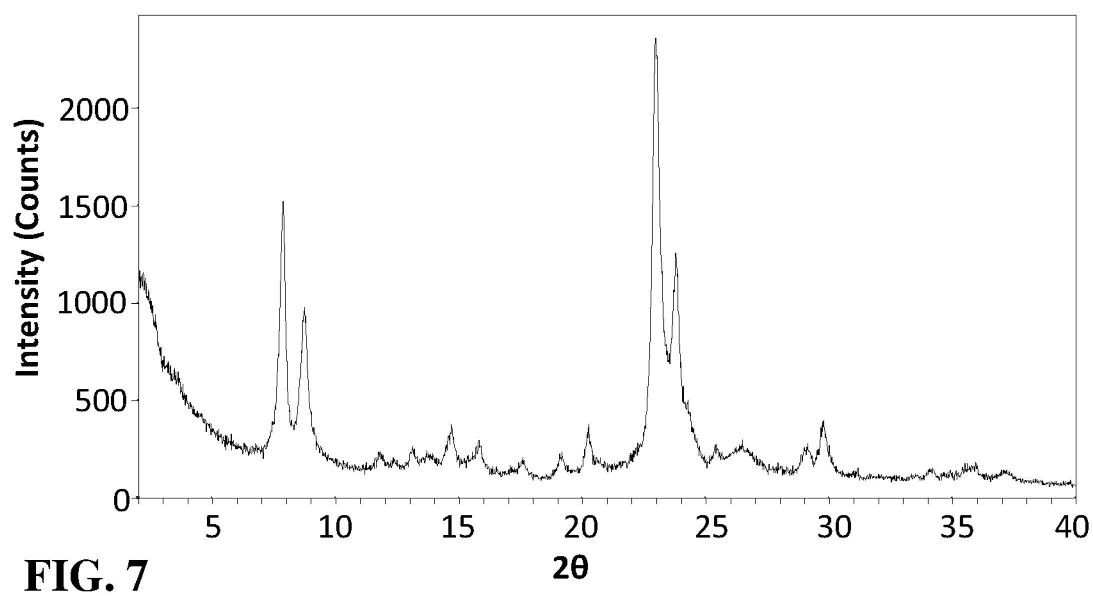
FIGS. 7, 8, and 9 are an XRD graph, a SEM image, and a TEM image of a ZSM-11 zeolite synthesized in Example A3 of this disclosure, respectively.
Figure 8:
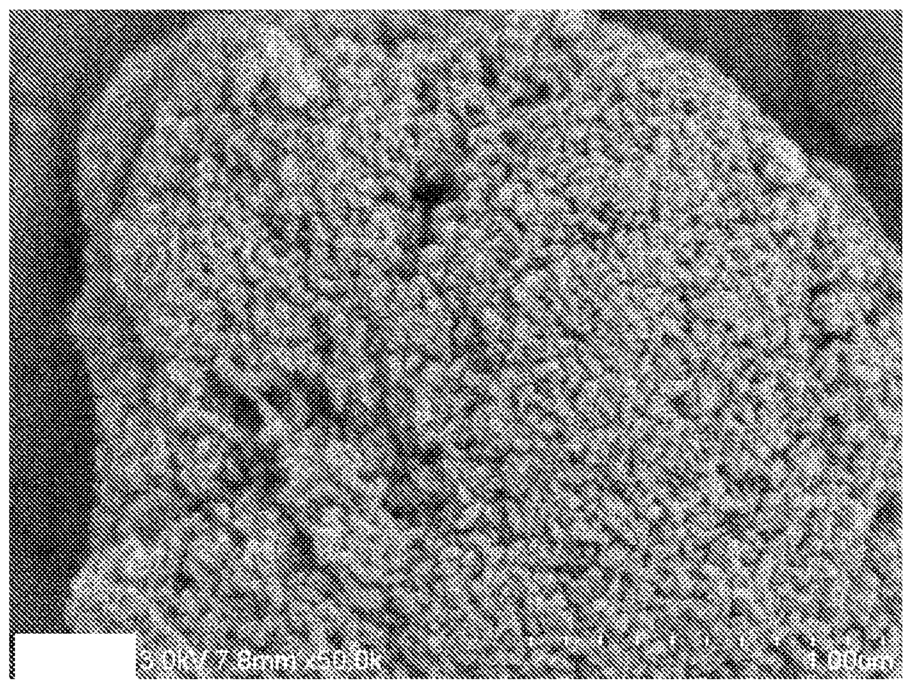
Figure 9:
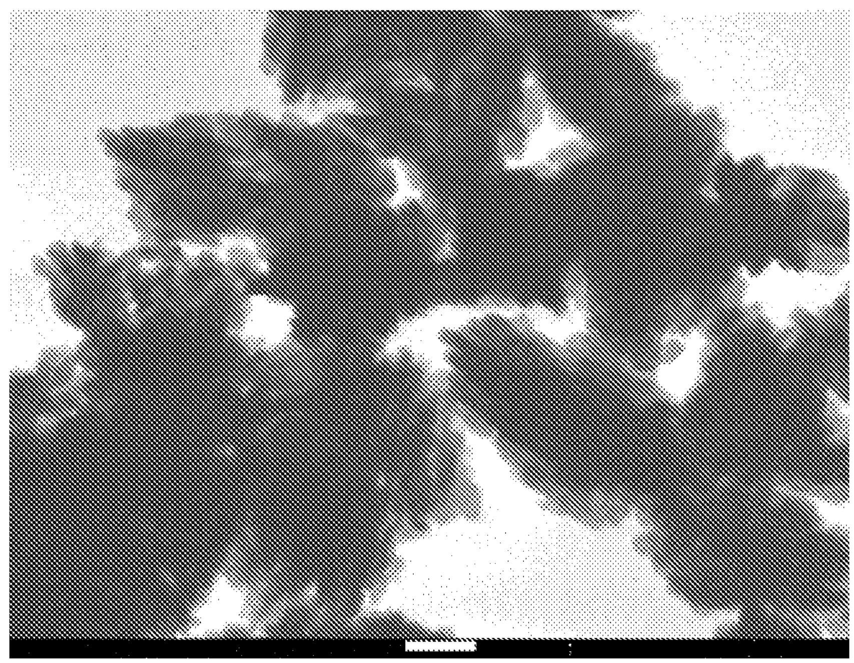

The mixture was reacted at 300° F. (148.9° C.) in an autoclave with stirring for 72 hours. The product was filtered, washed with DI water and dried at 250° F. (120° C.). The XRD graph in FIG. 7 of the resulting crystals shows the typical pattern of a ZSM-11 zeolite. A SEM image of the resulting crystals, shown in FIG. 8, indicates elongated-shaped agglomerates formed from crystallites, where the crystallites typically have sizes >50 nanometers. A TEM image of the resulting crystals, shown in FIG. 9, indicates a majority of the crystallites (primary particles) have primary dimension in the range from 50 to 200 nanometers, and aspect rations ≤3. The resulting crystals exhibited a silica/alumina molar ratio of ~28. A portion of the as-synthesized zeolite crystals were converted into the hydrogen form by three ion exchanges with ammonium nitrate solution at room temperature, followed by drying at 250° F. (120° C.) and calcination at 1000° F. (540° C.) for 6 hours. The hydrogen-form zeolite was measured to have an alpha value >1200, a hexane adsorption value of 90 mg/g, a total surface area of 446 $m^2/g$ and an external surface area of 90 $m^2/g$.

Example A-C1 (Comparative Example): Synthesis of a ZSM-5 Zeolite

A ZSM-5 zeolite with a $SiO_2/Al_2O_3$ molar ratio of ~26 and a crystallite size of ~100 nanometers was synthesized from a mixture of n-propylamine sol, silica, aluminum sulfate sol, and NaOH aqueous solution according to the procedures described in U.S. Pat. No. 4,526,879.

Part B: Fabrication of Catalyst Compositions

Example B1: Preparation of a First Catalyst Composition Comprising the ZSM-11 Zeolite of Example A1 and an Alumina Binder 80 parts (basis: calcined 538° C.) of the first ZSM-11 zeolite made in Example A1 were mixed with 20 parts of high surface area alumina and water in a muller. The alumina has a surface area in excess of 250 $m^2/g$ (basis: calcined 538° C.). The mixture was extruded and then dried at 121° C. overnight. The dried extrudate was calcined in nitrogen at 538° C. for 3 hours to decompose and remove the templating agent TBABr. The thus calcined extrudate was then humidified with saturated air and exchanged with 1 N ammonium nitrate to remove sodium (to a level of <500 wppm Na). After ammonium nitrate exchange, the extrudate was washed with DI water to remove residual nitrate ions prior to drying. The ammonium exchanged extrudate was then dried at 121° C. overnight and calcined in air at 538° C. for 3 hours to obtain a hydrogen-form catalyst composition comprising hydrogen-form ZSM-11 and alumina binder. The catalyst composition was measured to have a total surface area of 452 $m^2/g$, an external surface area of 178 $m^2/g$, a hexane sorption value of 90.5 mg/g, and an alpha value of 430.

Example B2: Preparation of a Second Catalyst Composition Comprising the ZSM-11 Zeolite of Example A3 and an Alumina Binder 80 parts (basis: calcined 538° C.) of the third ZSM-11 zeolite material from Example A3 were mixed with 20 parts of high surface area HSA alumina (basis: calcined 538° C.) and water in a muller. The mixture was extruded and then dried at 121° C. overnight. The dried extrudate was calcined in nitrogen at 538° C. for 3 hours to decompose and remove the templating agent TBABr. The thus calcined extrudate was then humidified with saturated air and exchanged with 1 N ammonium nitrate to remove sodium (to a level of <500 wppm Na). After ammonium nitrate exchange, the extrudate was washed with DI water to remove residual nitrate ions prior to drying. The ammonium exchanged extrudate was dried at 121° C. overnight and calcined in air at 538° C. for 3 hours to obtain a hydrogen-form catalyst composition comprising hydrogen-form ZSM-11 and alumina binder. The hydrogen-form catalyst composition was measured to have a total surface area of 430 $m^2/g$ and an external surface area of 157 $m^2/g$, and an alpha value of 1200.

Example B3: Preparation of a Third Catalyst Composition Comprising the ZSM-11 Zeolite of Example A2 and an Alumina Binder 80 parts (basis: calcined 538° C.) of the second ZSM-11 zeolite from Example A2 were mixed with 20 parts of high surface area HSA alumina (basis: calcined 538° C.) and water in a muller. The mixture was extruded and then dried at 121° C. overnight. The dried extrudate was then calcined in nitrogen at 538° C. for 3 hours to decompose and remove the templating agent TBABr. The thus calcined extrudate was then humidified with saturated air and exchanged with 1 N ammonium nitrate to remove sodium (to a level of <500 wppm Na). After ammonium nitrate exchange, the extrudate was washed with DI water to remove residual nitrate ions prior to drying. The ammonium exchanged extrudate was dried at 121° C. overnight and calcined in air at 538° C. for 3 hours to obtain a hydrogen-form catalyst composition comprising hydrogen-form ZSM-11 zeolite and alumina binder. The hydrogen-form catalyst composition was measured to have a total surface area of 432 $m^2/g$ and an external surface area of 200 $m^2/g$, a hexane sorption value of 85.5 mg/g, and an alpha value of 1000.

Example B4: Preparation of Fourth Catalyst Composition Comprising the ZSM-11 Zeolite of Example A2 and a Silica Binder 80 parts (basis: calcined 538° C.) of the ZSM-11 zeolite from Example A2 were mixed with 20 parts Ultrasil™ silica and a colloidal silica (silica basis: calcined 538° C.) and water in a muller. The mixture was extruded and then dried at 121° C. overnight. The dried extrudate was calcined in nitrogen at 538° C. for 3 hours to decompose and remove the templating agent TBABr. The thus calcined extrudate was then humidified with saturated air and exchanged with 1 N ammonium nitrate to remove sodium (to a level of <500 wppm Na). After ammonium nitrate exchange, the extrudate was washed with DI water to remove residual nitrate ions prior to drying. The ammonium exchanged extrudate was then dried at 121° C. overnight and calcined in air at 538° C. to obtain a hydrogen-form catalyst composition comprising hydrogen-form ZSM-11 zeolite and silica binder. The hydrogen-form catalyst composition was measured to have a hexane adsorption value of 80.7 mg/g, a total surface area of 430 $m^2/g$ and an external surface area of 181 $m^2/g$, and an alpha value of 1200.

Example B5: Preparation of a Fifth Catalyst Composition Comprising the ZSM-11 Zeolite of Example A2 and a Low Surface Area Alumina Binder 80 parts (basis: calcined 538° C.) of the ZSM-11 zeolite from Example A2 were mixed with 20 parts low surface area alumina (basis: calcined 538° C.) and water in a muller. The mixture was extruded and then dried at 121° C. overnight. The dried extrudate was calcined in nitrogen at 538° C. for 3 hours to decompose and remove the templating agent TBABr. The thus calcined extrudate was then humidified with saturated air and exchanged with 1 N ammonium nitrate to remove sodium (to a level of <500 wppm Na). After ammonium nitrate exchange, the extrudate was washed with DI water to remove residual nitrate ions prior to drying. The ammonium exchanged extrudate was then dried at 121° C. overnight and calcined in air at 538° C. to obtain a hydrogen-form catalyst composition comprising hydrogen-form ZSM-11 zeolite and alumina binder. The hydrogen-form catalyst composition was measured to have a hexane sorption value of 80.5 mg/g, a total surface area of 396 $m^2/g$, an external surface area of 148 $m^2/g$, and an alpha value of 930.

Example B6: Preparation of a Sixth Catalyst Composition Comprising the ZSM-11 Zeolite of Example A2, MCM-49 Zeolite, and an Alumina Binder 40 parts (basis: calcined 538° C.) of the ZSM-11 zeolite from Example A2 and 40 parts MCM-49 crystals were mixed with 20 parts of high surface area a HSA alumina (basis: calcined 538° C.) and water in a muller. The mixture was extruded and then dried at 121° C. overnight. The dried extrudate was calcined in nitrogen at 538° C. for 3 hours to decompose and remove the templating agent TBABr. The thus calcined extrudate was then humidified with saturated air and exchanged with 1 N ammonium nitrate to remove sodium (to a level of <500 wppm Na). After ammonium nitrate exchange, the extrudate was washed with DI water to remove residual nitrate ions prior to drying. The ammonium exchanged extrudate was then dried at 121° C. overnight and calcined in air at 538° C. for 3 hours to obtain a hydrogen-form catalyst composition comprising hydrogen-form ZSM-11, MCM-49, and alumina binder. The hydrogen-form catalyst composition was measured to have a total surface area of 467 $m^2/g$ and an external surface area of 170 $m^2/g$, a hexane sorption value of 86.5 mg/g, and an alpha value of 880.

Example B7: Preparation of a Seventh Catalyst Composition Comprising the ZSM-11 Zeolite of Example A2, the ZSM-5 Zeolite of Example A-C1, and an Alumina Binder 40 parts (basis: calcined 538° C.) of the ZSM-11 zeolite from Example A2 and 40 parts ZSM-5 zeolite from Example A-C1 were mixed with 20 parts of high surface area a HSA alumina (basis: calcined 538° C.) and water in a muller. The mixture was extruded and then dried at 121° C. overnight. The dried extrudate was calcined in nitrogen at 538° C. for 3 hours to decompose and remove the templating agent TBABr. The thus calcined extrudate was then humidified with saturated air and exchanged with 1 N ammonium nitrate to remove sodium (to a level of <500 wppm Na). After ammonium nitrate exchange, the extrudate was washed with DI water to remove residual nitrate ions prior to drying. The ammonium exchanged extrudate was then dried at 121° C. overnight and calcined in air at 538° C. for 3 hours to obtain a hydrogen-form catalyst composition comprising hydrogen-form ZSM-11, hydrogen-form ZSM-5, and alumina binder. The hydrogen-form catalyst composition was measured to have a total surface area of 422 $m^2/g$ with an external surface area of 182 $m^2/g$, a hexane sorption value of 84.9 mg/g, and an alpha value of 1000.

Example B8: Preparation of an Eighth Catalyst Composition by Steam-Treating the Second Catalyst Composition in Example B2

The second catalyst composition of Example B2 was steam treated at 700° F. (371° C.) for 3 hours and showed the following properties: a hexane sorption value of 84.1 mg/g, a total surface area of 350 $m^2/g$, and an alpha value of 800.

Example B9: Preparation of a Ninth Catalyst Composition by Steam-Treating the Third Catalyst Composition in Example B3

The third catalyst composition of Example B3 was steam treated at 700° F. (371° C.) for 3 hours and showed the following properties: a hexane sorption value of 78.5 mg/g, a total surface area of 415 $m^2/g$, and an alpha value of 720.

Example B-C1 (Comparative): Preparation of a Comparative Catalyst Composition Comprising ZSM-5 Zeolite and an Alumina Binder 80 parts (basis: calcined 538° C.) of the ZSM-5 zeolite from Example A-C1 were mixed with 20 parts of a HSA alumina (basis: calcined 538° C.) and water in a muller. The mixture was extruded and then dried at 121° C. overnight. The dried extrudate was calcined in nitrogen at 538° C. for 3 hours to decompose and remove the templating agent n-propyl amine. The thus calcined extrudate was humidified with saturated air and exchanged with 1 N ammonium nitrate to remove sodium in the catalyst (to a level of <500 wppm Na). After ammonium nitrate exchange, the extrudate was then washed with DI water to remove residual nitrate ions prior to drying. The ammonium exchanged extrudate was then dried at 121° C. overnight and calcined in air at 538° C. for 3 hours to obtain a hydrogen-form catalyst composition comprising hydrogen-form ZSM-5 and alumina binder. The hydrogen-form catalyst composition was measured to have a total surface area of 450 $m^2/g$, a hexane sorption value of 90 mg/g, and an alpha value of 900.

Part C: LPI Processes in the Presence of the Catalyst Compositions

A series of catalyst compositions prepared in the above examples in Part B having comparable extrudate sizes were tested in liquid-phase isomerization processes in Examples C1-C6 and C-C1 below. Each tested catalyst composition was first ground to 10/20 mesh. Then 1 gram of the ground catalyst composition was packed in an upflow tubular reactor. To remove moisture, the packed catalyst composition was then dried under flowing nitrogen gas, ramping at 2° C. per minute from room temperature to 240° C. and then held at 240° C. for one hour. Afterwards, an isomerization feed was supplied into the reactor from a bottoms inlet to contact the packed catalyst composition. Isomerization conditions were set at 265 psig (1827 kPa, gauge) and 240° C. and a WHSV varying from 2.5 to 15 $hour^{-1}$. No molecular hydrogen was fed into the reactor. The isomerization feed had the following composition, based on the total weight of the isomerization feed: 13 wt % ethylbenzene, 1.5 wt % C8-C9 non-aromatics, 1.5 wt % of p-xylene, 19 wt % of o-xylene, and 66 wt % of m-xylene. The isomerization product mixture effluent exiting the reactor from the top was collected and analyzed for its composition. In the reported results, p-xylene selectivity in product is defined as the concentration of p-xylene among all xylenes in the isomerization product mixture effluent. Xylenes loss (Lx (%)) is calculated as follows: Lx=100%*(W1−W2)/W1, where W1 is the total weight of xylenes in the isomerization feed, and W2 is the total weight of xylenes in the isomerization product mixture effluent.

Example C-C1 (Comparative): LPI in the Presence of the Catalyst Composition of Example B-C1

The catalyst composition of Example B-C1 above, comprising a HSA alumina binder and a ZSM-5 zeolite having mid-size crystallites and a $SiO_2/Al_2O_3$ molar ratio of ~26 was tested. WHSV and results are included in TABLE C-C1.

TABLE C-C1

| WHSV ($hour^{-1}$) | 2.5 | 5 | 10 | 15 |
|---|---|---|---|---|
| p-Xylene selectivity in product (%) | 23.7 | 22.6 | 19.4 | 16.6 |
| Ethylbenzene conversion (%) | 3.8 | 1.1 | 0.8 | 0.4 |
| Benzene yield (wppm) | 978 | 327 | 309 | 79 |
| A9+ yield (wppm) | 4212 | 497 | ~0 | ~0 |
| Toluene yield (wt %) | 0.20 | 0.06 | 0.03 | 0.02 |
| Xylenes loss (%) | 0.23 | 0.06 | 0.01 | 0.02 |

Example C1: LPI in the Presence of the Catalyst Composition of Example B3

The catalyst composition of Example B3 above, comprising a HSA alumina binder and a ZSM-11 zeolite having small crystallites and a $SiO_2/Al_2O_3$ molar ratio of ~25 was tested. Results and reaction conditions are shown in TABLE I.

TABLE I

| WHSV ($hour^{-1}$) | 2.5 | 5 | 10 | 15 |
|---|---|---|---|---|
| p-Xylene selectivity in product (%) | 23.6 | 23.6 | 22.8 | 21.3 |
| Ethylbenzene conversion (%) | 1.8 | 1.0 | 0.6 | 0.4 |
| Benzene yield (wppm) | 936 | 308 | 312 | 76 |
| A9+ yield (wppm) | 707 | 253 | ~0 | ~0 |
| Toluene yield (wt %) | 0.11 | 0.03 | 0.03 | 0.02 |
| Xylenes loss (%) | 0.04 | 0.02 | 0.04 | 0.04 |

The catalyst composition of Example B3 above, comprising a HSA alumina binder and a ZSM-11 zeolite having small crystallites and a $SiO_2/Al_2O_3$ molar ratio of ~25 was tested. WHSV and results are shown in TABLE I.

From the data in TABLE C-C1 and TABLE I, the advantages of the inventive catalyst composition of Example B3 over the comparative catalyst composition of Example B-C1 are many and very significant: (i) at both WHSV of 2.5 and 5 $hour^{-1}$, the inventive catalyst composition of Example B3 resulted in much lower xylenes loss; (ii) at both WHSV of 2.5 and 5 $hour^{-1}$, the inventive catalyst composition of Example B3 resulted in much lower A9+ yield; (iii) at both WHSV of 2.5 and 5 $hour^{-1}$, the inventive catalyst composition of Example B3 resulted in much lower toluene yield as well; and (iv) at high WHSV≥5 $hour^{-1}$, the inventive catalyst composition of Example B3 resulted in much higher p-xylene selectivity in the product mixture effluent, showing much higher isomerization activity than the comparative catalyst composition of Example B-C1. Particularly, the inventive ZSM-11-containing catalyst composition of Example B3 is far superior to the comparative ZSM-5-based catalyst composition of Example B-C1 at WHSV≥5 $hour^{-1}$, and even more so at WHSV≥10 up to 15 $hour^{-1}$, primarily due to the much higher p-xylene selectivity at such high WHSV.

Given that both the catalyst compositions of Example B3 and comparative Example B-C1 contain HSA alumina as a binder, this example clearly shows the advantages of ZSM-11 zeolite over ZSM-5 zeolite in catalyzing a LPI process, especially at relatively low WHSV from 2.5 to 5 $hour^{-1}$.

Example C2: LPI in the Presence of the Catalyst Composition of Example B2

The catalyst composition of Example B2 above, comprising a HSA alumina binder and a ZSM-11 zeolite having mid-size crystallites and a $SiO_2/Al_2O_3$ molar ratio of ~28 was tested. WHSV and results are shown in TABLE II.

TABLE II

| WHSV ($hour^{-1}$) | 2.5 | 5 | 10 | 15 |
|---|---|---|---|---|
| p-Xylene selectivity in product (%) | 23.5 | 22.8 | 20.0 | 17.1 |
| Ethylbenzene conversion (%) | 1.9 | 1.1 | 0.6 | 0.5 |
| Benzene yield (wppm) | 902 | 482 | ~0 | ~0 |
| A9+ yield (wppm) | 2099 | 416 | ~0 | ~0 |
| Toluene yield (wt %) | 0.10 | 0.03 | 0.01 | ~0 |
| Xylenes loss (%) | 0.13 | ~0 | ~0 | ~0 |

From the data in TABLE C-C1 and TABLE II, one can observe the following advantages of the inventive catalyst composition of Example B2 over the comparative catalyst composition of Example B-C1: (i) at both WHSV of 2.5 and 5 $hour^{-1}$, the inventive catalyst composition of Example B2 resulted in much lower xylenes loss; (ii) at both WHSV of 2.5 and 5 $hour^{-1}$, the inventive catalyst composition of Example B2 resulted in much lower A9+ yield; (iii) at both WHSV of 2.5 and 5 $hour^{-1}$, the inventive catalyst composition of Example B2 resulted in much lower toluene yield as well; and (iv) at high WHSV≥5 $hour^{-1}$, the inventive catalyst composition of Example B2 resulted in slightly higher p-xylene selectivity in the product mixture effluent, showing slightly higher isomerization activity than the comparative catalyst composition of Example B-C1. Thus, the inventive catalyst composition of Example B2 is superior to the ZSM-5-based catalyst composition of comparative Example B-C1.

From the data in TABLE I and TABLE II, one can see that the inventive catalyst composition of Example B2 resulted in higher xylenes loss at WHSV of 2.5 $hour^{-1}$, much higher A9+ yield at both WHSV of 2.5 and 5.0 $hour^{-1}$, and much lower p-xylene selectivity at high WHSV of 5 and 10 $hour^{-1}$. As such, the catalyst composition of Example B3 is superior to the catalyst composition of Example B2. It is believed that the smaller crystallize size of the ZSM-11 zeolite in the catalyst composition of Example B3 resulted in the higher performance of the catalyst composition. The ZSM-11 zeolites in both catalysts have similar $SiO_2/Al_2O_3$ molar ratios. Thus, it is preferable for the ZSM-11 zeolite to have a crystallite size ≤80 nanometers, more preferable ≤50 nanometers, still more preferable ≤30 nanometers, especially for the purpose of making an LPI isomerization catalyst composition.

Example C3: LPI in the Presence of the Catalyst Composition of Example B1

The catalyst composition of Example B1 above, comprising a HSA alumina binder and a ZSM-11 zeolite having small crystallites and a SiO2/Al2O3 molar ratio of 50 was tested. WHSV and results are shown in TABLE III.

TABLE III

| WHSV ($hour^{-1}$) | 2.5 | 5 | 10 | 15 |
|---|---|---|---|---|
| p-Xylene selectivity in product (%) | 23.6 | 22.3 | 18.5 | 15.2 |
| Ethylbenzene conversion (%) | 1.0 | 0.5 | 0.3 | 0.2 |
| Benzene yield (wppm) | 530 | ~0 | ~0 | ~0 |
| A9+ yield (wppm) | 396 | ~0 | ~0 | ~0 |
| Toluene yield, wt % | 0.03 | 0.01 | ~0 | ~0 |
| Xylenes loss (%) | ~0 | ~0 | ~0 | ~0 |

From the data in TABLE C-C1 and TABLE III, one can observe the following advantages of the inventive catalyst composition of Example B1 over the comparative catalyst composition of Example B-C1: (i) at both WHSV of 2.5 and 5 $hour^{-1}$, the inventive catalyst composition of Example B1 resulted in much lower xylenes loss; (ii) at both WHSV of 2.5 and 5 $hour^{-1}$, the inventive catalyst composition of Example B1 resulted in much lower A9+ yield; and (iii) at both WHSV of 2.5 and 5 $hour^{-1}$, the inventive catalyst composition of Example B1 resulted in much lower toluene yield as well. Thus, the inventive catalyst composition of Example B1 is superior to the ZSM-5-based catalyst composition of comparative Example B-C1.

From the data in TABLE I and TABLE IV, one can see that the inventive catalyst composition of Example B1 resulted in much lower p-xylene selectivity at high WHSV of 5 and 10 $hour^{-1}$ than the inventive catalyst composition of Example B3. As such, the catalyst composition of Example B3 is superior to the catalyst composition of Example B1. Without intending to be bound by a particular theory, it is believed that the much higher $SiO_2/Al_2O_3$ molar ratio the ZSM-11 zeolite in the catalyst composition of Example B1 resulted in the lower isomerization activity than the catalyst composition of Example B3. The ZSM-11 zeolites in both catalyst compositions have comparable crystallite sizes. Accordingly, it is preferable for the ZSM-11 zeolite to have a $SiO_2/Al_2O_3$ molar ratio in a range from 20 to 40, more preferable from 20 to 30, in a ZSM-11 zeolite, especially for the purpose of making a LPI isomerization catalyst composition.

Example C4: LPI in the Presence of the Catalyst Composition of Example B4

The catalyst composition of Example B4 above, comprising a silica binder and a ZSM-11 zeolite having small crystallites and a $SiO_2/Al_2O_3$ molar ratio of ~25 was tested. WHSV and results are shown in TABLE IV below.

TABLE IV

| WHSV ($hour^{-1}$) | 2.5 | 5 | 10 | 15 |
|---|---|---|---|---|
| p-Xylene selectivity in product (%) | 23.7 | 23.7 | 23.2 | 22.1 |
| Ethylbenzene conversion (%) | 1.9 | 0.9 | 0.6 | 0.3 |
| Benzene yield (wppm) | 1177 | 328 | 327 | ~0 |
| A9+ yield (wppm) | 779 | 255 | ~0 | ~0 |
| Toluene yield, wt % | 0.07 | 0.03 | 0.03 | 0.01 |
| Xylenes loss (%) | 0.02 | 0.03 | 0.04 | 0.01 |

From the data in TABLE C-C1 and TABLE IV, one can observe the following advantages of the inventive catalyst composition of Example B4 over the comparative catalyst composition of Example B-C1: (i) at both WHSV of 2.5 and 5 $hour^{-1}$, the inventive catalyst composition of Example B4 resulted in much lower xylenes loss; (ii) at both WHSV of 2.5 and 5 $hour^{-1}$, the inventive catalyst composition of Example B4 resulted in much lower A9+ yield; (iii) at both WHSV of 2.5 and 5 $hour^{-1}$, the inventive catalyst composition of Example B2 resulted in much lower toluene yield as well; and (iv) at high WHSV≥5 $hour^{-1}$, the inventive catalyst composition of Example B4 resulted in significantly higher p-xylene selectivity in the product mixture effluent, showing significantly higher isomerization activity than the comparative catalyst composition of Example B-C1. Thus, the inventive catalyst composition of Example B4 is much superior to the ZSM-5-based catalyst composition of comparative Example B-C1. Particularly, the inventive ZSM-11-containing catalyst composition of Example B4 is far superior to the comparative ZSM-5-based catalyst composition of Example B-C1 at WHSV≥5 $hour^{-1}$, and even more so at WHSV≥10 up to 15 $hour^{-1}$, primarily due to the much higher p-xylene selectivity at such high WHSV.

From the data in TABLE I and TABLE IV, one can see that the inventive catalyst compositions of Examples B3 and B4 had very similar performances in the LPI process tests. This shows that the same small-crystallite ZSM-11 zeolite having a $SiO_2/Al_2O_3$ molar ratio of ~25 can be bound with either HSA alumina or silica to produce high-activity, high-performance catalyst composition of this disclosure.

Example C5: LPI in the Presence of the Catalyst Composition of Example B5

The catalyst composition of Example B5 above, comprising a LSA alumina binder and a ZSM-11 zeolite having small crystallites and a $SiO_2/Al_2O_3$ molar ratio of ~25 was tested. WHSV and results are shown in TABLE V below.

TABLE V

| WHSV (hour$^{-1}$) | 2.5 | 5 | 10 | 15 |
|---|---|---|---|---|
| p-Xylene selectivity in product (%) | 23.7 | 23.5 | 22.7 | 21.2 |
| Ethylbenzene conversion (%) | 1.9 | 1.0 | 0.5 | 0.3 |
| Benzene yield (wppm) | 1051 | 600 | ~0 | ~0 |
| A9+ yield (wppm) | 1306 | 482 | ~0 | ~0 |
| Toluene yield, wt % | 0.08 | 0.02 | ~0 | ~0 |
| Xylenes loss (%) | 0.06 | ~0 | ~0 | ~0 |

From the data in TABLE C-C1 and TABLE V, one can observe the following advantages of the inventive catalyst composition of Example B5 over the comparative catalyst composition of Example B-C1: (i) at both WHSV of 2.5 and 5 hour$^{-1}$, the inventive catalyst composition of Example B5 resulted in much lower xylenes loss; (ii) at both WHSV of 2.5 and 5 hour$^{-1}$, the inventive catalyst composition of Example B5 resulted in much lower A9+ yield; (iii) at both WHSV of 2.5 and 5 hour$^{-1}$, the inventive catalyst composition of Example B5 resulted in much lower toluene yield as well; and (iv) at high WHSV≥5 hour$^{-1}$, the inventive catalyst composition of Example B5 resulted in significantly higher p-xylene selectivity in the product mixture effluent, showing significantly higher isomerization activity than the comparative catalyst composition of Example B-C1. Thus, the inventive catalyst composition of Example B5 is much superior to the ZSM-5-based catalyst composition of comparative Example B-C1. Particularly, the inventive ZSM-11-containing catalyst composition of Example B5 is far superior to the comparative ZSM-5-based catalyst composition of Example B-C1 at WHSV≥5 hour$^{-1}$, and even more so at WHSV≥10 up to 15 hour$^{-1}$, primarily due to the much higher p-xylene selectivity at such high WHSV.

From the data in TABLE I and TABLE V, one can see that the inventive catalyst compositions of Examples B3 and B5 had very similar performances in the LPI process tests. This shows that the same small-crystallite ZSM-11 zeolite having a $SiO_2/Al_2O_3$ molar ratio of ~25 can be bound with either HSA alumina or LSA alumina to produce high-activity, high-performance catalyst composition of this disclosure. Nonetheless, the catalyst composition of Example B3 showed slightly higher performance, especially in terms of xylene selectivity at all WHSV, benzene yield at WHSV of 2.5 and 5 hour$^{-1}$, and A9+ yield at 2.5 and 5 hour$^{-1}$, compared to the catalyst composition of Example B5, presumably due to the higher surface area of the alumina binder used in the catalyst composition of Example B3.

Example C6: LPI in the Presence of the Catalyst Composition of Example B6

The catalyst composition of Example B6 above, comprising a HSA alumina binder, a ZSM-11 zeolite having small crystallites and a $SiO_2/Al_2O_3$ molar ratio of ~25, and a MCM-49 zeolite was tested. WHSV and results are shown in TABLE VI below.

TABLE VI

| WHSV(hour$^{-1}$) | 2.5 | 5 | 10 | 15 |
|---|---|---|---|---|
| p-Xylene selectivity in product (%) | 23.6 | 23.0 | 20.2 | 17.4 |
| Ethylbenzene conversion (%) | 2.5 | 1.1 | 0.6 | 0.3 |
| Benzene yield (wppm) | 1290 | 334 | 350 | 86.6 |
| A9+ yield (wppm) | 1687 | 226 | ~0 | ~0 |
| Toluene yield, wt % | 0.17 | 0.03 | 0.02 | 0.02 |
| Xylenes loss (%) | 0.16 | 0.02 | 0.04 | 0.03 |

From the data in TABLE C-C1 and TABLE VI, one can observe the following advantages of the inventive catalyst composition of Example B6 over the comparative catalyst composition of Example B-C1: (i) at both WHSV of 2.5 and 5 hour$^{-1}$, the inventive catalyst composition of Example B6 resulted in much lower xylenes loss; (ii) at both WHSV of 2.5 and 5 hour$^{-1}$, the inventive catalyst composition of Example B6 resulted in much lower A9+ yield; and (iii) at high WHSV≥5 hour$^{-1}$, the inventive catalyst composition of Example B5 resulted in slightly higher p-xylene selectivity in the product mixture effluent, showing slightly higher isomerization activity than the comparative catalyst composition of Example B-C1. Thus, the inventive catalyst composition of Example B5 is superior to the ZSM-5-based catalyst composition of comparative Example B-C1.

From the data in TABLE I and TABLE VI, one can see that the inventive catalyst composition of Examples B3 is superior to the catalyst composition of Example B6 in terms of xylenes loss, toluene yield, A9+ yield, benzene yield, and p-xylene selectivity, especially A9+ yield at WHSV of 2.5 and 5 hour$^{-1}$, and especially p-xylene selectivity at WHSV of ≥5 hour$^{-1}$, particularly at 10 and 15 hour$^{-1}$. The presence of MCM-49 at 50 wt % in the zeolite mixture may have reduced xylenes loss, toluene yield, A9+ yield, benzene yield, and p-xylene selectivity, but it appears to have improved EB conversion, compared to the catalyst composition of Example B3.

The compositions of the zeolites and catalyst compositions in the above examples, and the relationship of the above examples are provided in TABLE VII below.

Figure 10:
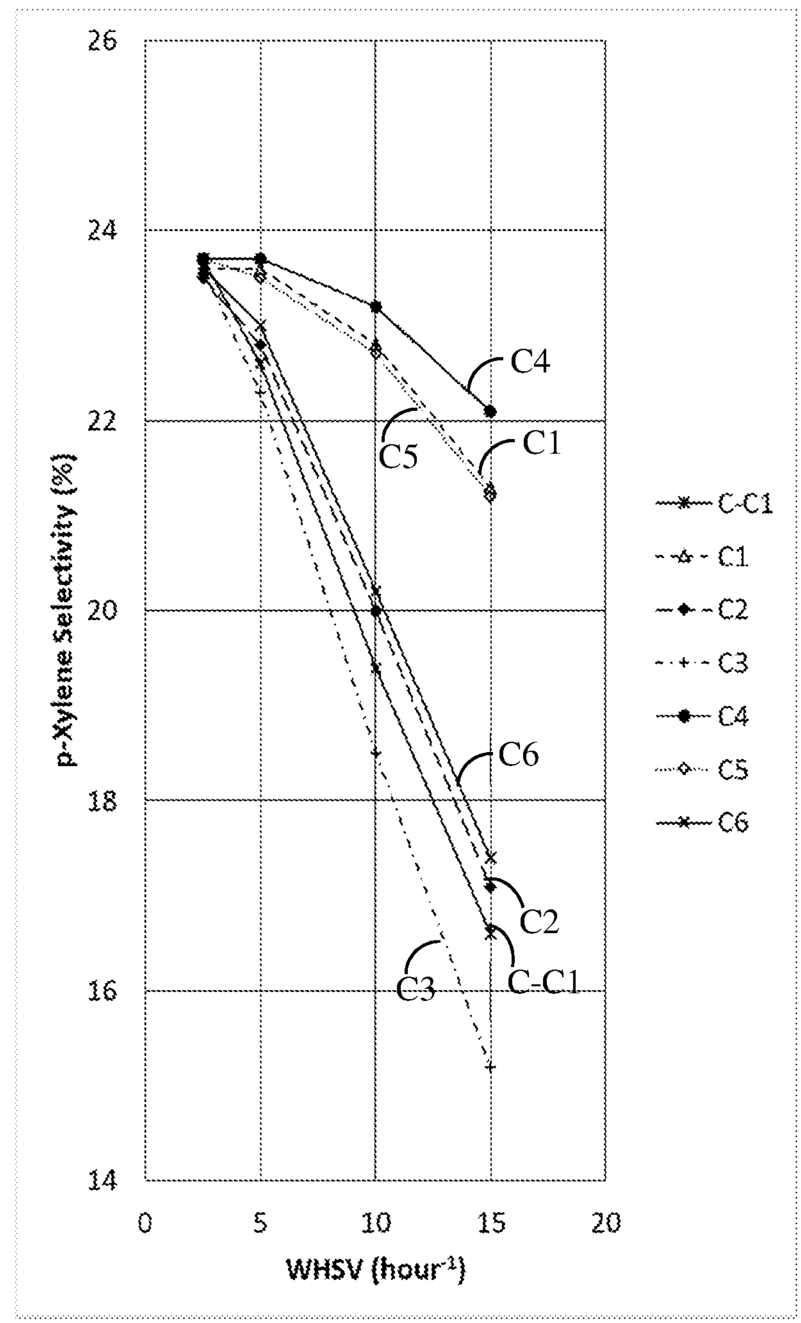
FIG. 10 is a graph showing p-xylene selectivity as a function of WHSV in exemplary processes in this disclosure.
Figure 11:
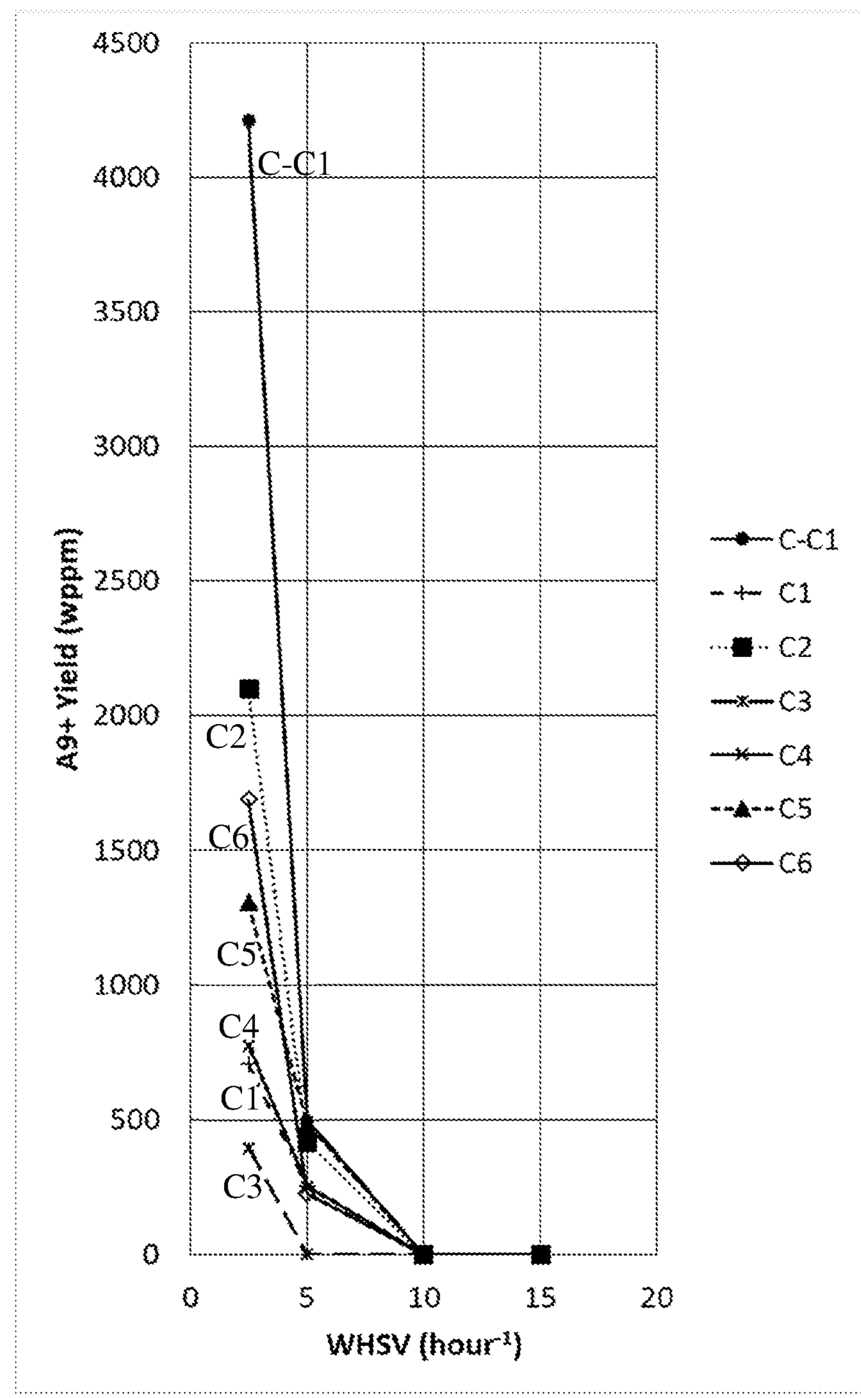
FIG. 11 is a graph showing A9+ yield as a function of WHSV in the same exemplary processes illustrated in FIG. 10.
Figure 12:
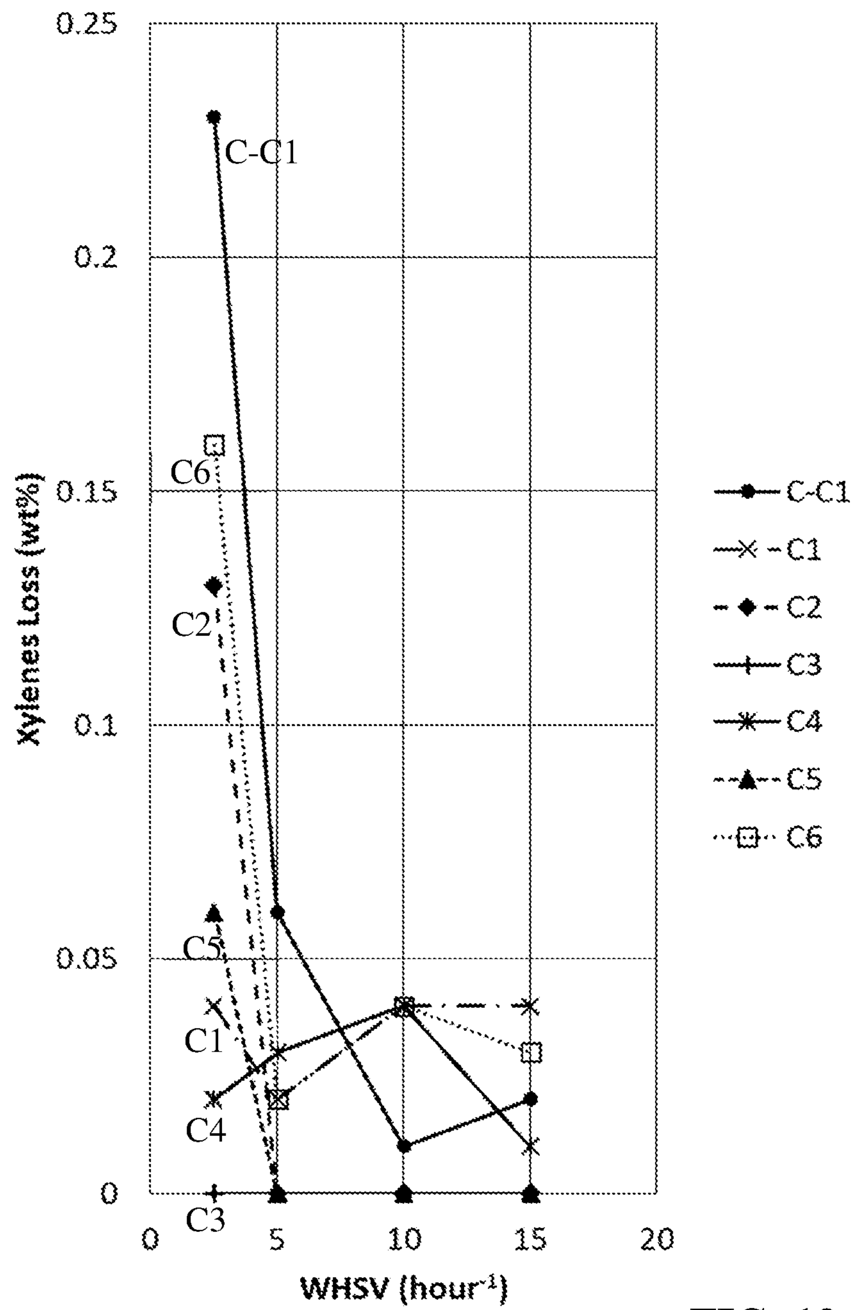
FIG. 12 is a graph showing xylenes loss as a function of WHSV in the same exemplary processes illustrated in FIGS. 10 and 11.

A portion of the data in TABLES C-C1 and I to VI are also plotted into the graphs in FIGS. 10, 11, and 12.

FIG. 10 shows p-xylene selectivity as a function of WHSV in all process Examples C-C1 and C1 to C6. As can be clearly seen from this figure, inventive processes in Examples C1 (using the catalyst composition of Example B3), C2 (using the catalyst composition of Example B2), C4 (using the catalyst composition of Example B4), C5 (using the catalyst composition of Example B5), and C6 (using the catalyst composition of Example B6), in the whole tested WHSV range, from 2.5 to 15 hour$^{-1}$, exhibited p-xylene selectivity consistently higher than the comparative process in Example C-C1 (using a ZSM-5 based catalyst composition). Only the process in Example C3 (using the catalyst composition of Example B1) showed lower p-xylene selectivity than the comparative process in Example C-C1 at WHSV≥5 hour$^{-1}$. Specifically, processes in Examples C1, C4, and C5 consistently exhibited very high p-xylene selectivity in the full WHSV test range from 2.5 to 15 hour$^{-1}$. The catalyst compositions used in these examples, i.e., those in Examples B3, B4, and B5, respectively, are highly advantageous in high throughput, high WHSV liquid-phase isomerization processes for converting xylenes.

FIG. 11 shows A9+(i.e., C9+ aromatic hydrocarbons) yield as a function of WHSV in all process Examples C-C1 and C1 to C6. The production of A9+ due to side reactions is highly undesirable in a C8 aromatics isomerization process. As can be clearly seen from this figure, all inventive processes in Examples C1 to C6, in low WHSV range from 2.5 to 5.0 hour$^{-1}$, exhibited A9+ yield consistently lower than the comparative process in Example C-C1. It is also notable that processes C1, C4, and C5, which stand out in FIG. 10 due to high p-xylene selectivity across the WHSV test range and particularly ≥10 hour$^{-1}$, also stand out in FIG. 11 showing very low A9+ yield at low WHSV at 2.5 and 5.0 hour$^{-1}$. Clearly the catalyst compositions of Examples B3, B4, and B5, which were used in these exemplary processes, are advantageous even at relatively low WHSV of ≤5.0 hour$^{-1}$.

FIG. 12 shows xylenes loss as a function of WHSV in all process Examples C-C1 and C1 to C6. Xylenes loss due to side reactions is highly undesirable in a C8 aromatics isomerization process. As can be clearly seen from this figure, all inventive processes in Examples C1 to C6, in low WHSV range from 2.5 to 5.0 hour$^{-1}$, exhibited xylenes loss significantly lower than the comparative process in Example C-C1. It is also notable that processes C1, C4, and C5, which stand out in FIGS. 10 and 11, also stand out in FIG. 12 showing very low xylenes loss at low WHSV at 2.5 and 5.0 hour$^{-1}$. Clearly the catalyst compositions of Examples B3, B4, and B5, which were used in these exemplary processes, are advantageous even at relatively low WHSV of ≤5.0 hour$^{-1}$ from this additional perspective.

TABLE VII

| | First Zeolite | | | | | | |
|---|---|---|---|---|---|---|---|
| Example No. | Type | $SiO_2/Al_2O_3$ Ratio | Crystallite Size (nm) | Second Zeolite | Binder | Zeolite of Example | Catalyst Composition of Example |
| A1 | ZSM-11 | ~50 | ≤40 | — | — | — | — |
| A2 | ZSM-11 | ~25 | ≤40 | — | — | — | — |
| A3 | ZSM-11 | ~28 | 50-200 | — | — | — | — |
| A-C1 | ZSM-5 | ~26 | ~100 | — | — | — | — |
| B1 | ZSM-11 | ~50 | ≤40 | — | HSA-$Al_2O_3$ | A1 | — |
| B2 | ZSM-11 | ~28 | 50-200 | — | HSA-$Al_2O_3$ | A3 | — |
| B3 | ZSM-11 | ~25 | ≤40 | — | HSA-$Al_2O_3$ | A2 | — |
| B4 | ZSM-11 | ~25 | ≤40 | — | $SiO_2$ | A2 | — |
| B5 | ZSM-11 | ~25 | ≤40 | — | LSA-$Al_2O_3$ | A2 | — |
| B6 | ZSM-11 | ~25 | ≤40 | MCM-49 | HSA-$Al_2O_3$ | A2 | — |
| B7 | ZSM-11 | ~25 | ≤40 | — | HSA-$Al_2O_3$ | A2 | — |
| B8 | ZSM-11 | ~28 | 50-200 | — | HSA-$Al_2O_3$ | B2 steamed | — |
| B9 | ZSM-11 | ~25 | ≤40 | — | HSA-$Al_2O_3$ | B3 Steamed | — |
| B-C1 | ZSM-5 | ~26 | ~100 | — | HSA-$Al_2O_3$ | A-C1 | — |
| C1 | ZSM-11 | ~25 | ≤40 | — | HSA-$Al_2O_3$ | A2 | B3 |
| C2 | ZSM-11 | ~28 | 50-200 | — | HSA-$Al_2O_3$ | A3 | B2 |
| C3 | ZSM-11 | ~50 | ≤40 | — | HSA-$Al_2O_3$ | A1 | B1 |
| C4 | ZSM-11 | ~25 | ≤40 | — | $SiO_2$ | A2 | B4 |
| C5 | ZSM-11 | ~25 | ≤40 | — | LSA-$Al_2O_3$ | A2 | B5 |
| C6 | ZSM-11 | ~25 | ≤40 | MCM-49 | HSA-$Al_2O_3$ | A2 | B6 |
| C-C1 | ZSM-5 | ~26 | ~100 | — | HSA-$Al_2O_3$ | A-C1 | B-C1 |

Example C7: Evaluation of Catalyst Aging in LPI Processes

To evaluate catalyst aging, an inventive catalyst composition consisting essentially of a ZSM-11 zeolite and an alumina binder corresponding to Example B3 above was tested according to the same procedure as in the preceding examples C1 to C6 except: (i) a larger down-flow tubular reactor was used, in which ~30-40 grams of the catalyst composition was packed; (ii) the isomerization feed was fed from the top of the reactor; (iii) the isomerization product mixture effluent exited from the bottom of the reactor; and (iv) the WHSV was fixed at 5 hour$^{-1}$. The test reaction was allowed to run over a period of over 20 days. For comparison, a comparative catalyst composition consisting essentially of a ZSM-5 zeolite and an alumina binder corresponding to Example B-C1 was evaluated for a comparable period under the same test conditions except the WHSV was fixed at 4 hour$^{-1}$. The catalyst deactivation rates of both catalysts were calculated from the test data and reported in TABLE VIII below. The catalyst deactivation is calculated as p-xylene selectivity change (i.e., S(pX)1−S(pX)2, where S(pX)1 is the initial p-xylene selectivity in the product mixture effluent, and S(pX)2 is the end p-xylene selectivity in the product mixture effluent after a month on the stream). Thus, the higher (S(pX)1−S(pX)2) per month is, the higher the reduction of p-xylene selectivity over a month, and the faster the catalyst deactivates.

TABLE VIII

| Catalyst Composition | (S(pX)1 − S(pX)2) per month | WHSV (hour$^{-1}$) |
|---|---|---|
| Alumina-bound ZSM-11 | 0.01% | 5 |
| Alumina-bound ZSM-5 | 0.9% | 4 |

Data in TABLE VIII clearly show that the inventive alumina-bound ZSM-11 catalyst composition demonstrated far superior performance in terms of catalyst deactivation rate than the comparative ZSM-5-based catalyst composition. At comparable WHSV, the inventive catalyst composition resulted in p-xylene selectivity reduction per month that is almost two orders of magnitude lower than that of the comparative catalyst composition. This again clearly shows the advantage of ZSM-11 zeolite-containing catalyst composition over a ZSM-5-based catalyst composition, especially in liquid phase isomerization.

This disclosure can further include the following non-limiting embodiments.

A1. A zeolite material of the MEL framework type comprising a plurality of crystallites, wherein at least 75% of the crystallites have crystallite size of at most 200 nanometers, preferably at most 180 nanometers, preferably at most 160 nanometers, preferably at most 150 nanometers, preferably at most 140 nanometers, preferably at most 120 nanometers, preferably at most 100 nanometers, preferably at most 80 nanometers, and more preferably at most 50 nanometers, as determined by transmission electron scope image analysis.

A2. The zeolite material of A1, wherein the crystallites have an aspect ratio from 1 to 5, preferably from 1 to 3, more preferably from 1 to 2.

A3. The zeolite material of A1 or A2, having a silica to alumina molar ratio of from 10 to 60, preferably from 15 to 50, more preferably 20 to 30.

A4. The zeolite material of any of A1 to A3, having a BET total surface area of from 300 to 600 $m^2$/g, preferably from 400 to 500 $m^2$/g, more preferably from 400 to 475 $m^2$/g.

A5. The zeolite material of any of A1 to A4, having a mesopore area of at least 15% of the total surface area, preferably at least 20% of the total surface area, and more preferably at least 25% of the total surface area.

A6. The zeolite material of any of A1 to A5, wherein at least a portion of the crystallites aggregate to form a plurality of agglomerates.

A7. The zeolite material of any of A1 to A6, further exhibiting one or more of the following:

(I) a hexane sorption value from 90 to 110 mg/g; and (II) an alpha value from 500 to 3000.

A8. The zeolite material of any of A1 to A7, wherein the crystallites are substantially spherical in shape.

A9. The zeolite material of any of A1 to A6, wherein the crystallites are substantially rod in shape.

A10. The zeolite material of any of A1 to A9, which is as synthesized.

A11. The zeolite material of any of A1 to A9, which is calcined.

B1. A process for making the zeolite material of any of A1 to A11, the process comprising:

(I) forming a synthesis mixture from a silicon source, an aluminum source, an alkali metal (M) hydroxide, a source of a structure directing agent (SDA) selected from the group consisting of tetrabutyl ammonium ("TBA") compounds, water, and optionally seed crystals, wherein the synthesis mixture has an overall composition having the following molar ratios:

| | |
|---|---|
| SiO2:Al2O3 | 15-70 |
| $OH^-$:Si | 0.05-0.5 |
| $M^+$:Si | 0.2-0.4 |
| SDA:Si | 0.01-0.1 |
| $H_2O$:Si | ≤20 |

(II) subjecting the synthesis mixture to crystallization conditions which include heating the synthesis mixture at a temperature in the range of from 100° C. to 150° C. to form a reacted mixture comprising a solid material; and (III) obtaining the zeolite material from the reacted mixture.

B2. The process of B1, wherein the silicon source is a precipitation silica.

B3. The process of B1 or B2, wherein the aluminum source is a sodium aluminate solution and/or an aluminum sulfate solution.

B4. The process of any of B1 to B3, wherein the SDA source is selected from the group consisting of TBA hydroxide, TBA chloride, TBA fluoride, TBA bromide, alkyldiamines having 7-12 carbon atoms, and mixtures and combinations thereof.

B5. The process of any of B1 to B4, wherein step (III) comprises:

(IIIa) filtering the reacted mixture to recover the solid material;

(IIIb) washing the solid material; and (IIIc) drying the washed solid material.

B6. The process of B5, wherein the process further comprises:

(IIId) subjecting the washed solid material obtained from step (Ib) or the dried and/or calcined solid material to an ion exchange treatment using an ammonium salt to at least partly remove alkali metal cation M+ to obtain an ion-exchanged solid material; and (IIIe) calcining the ion-exchanged solid material at a temperature of at least 500° C. for a period of at least 1 hour.

B7. The process of any of B1 to B6, further comprising:

(IV) mixing the zeolite material obtained in step (III) with a binder, optionally a second zeolite material, optionally a hydrogenation metal, and optionally water;

(V) forming the mixture obtained in step (IV) to desired shape; and (VI) drying and/or calcining the formed mixture obtained in step (V) to obtain a catalyst comprising the zeolite material and the binder.

B8. The process of B7, wherein step (V) comprises extruding the mixture.

B9. The process of B7 or B8, further comprising, between step (V) and (VI), the following:

(Va) ion-exchanging the formed mixture with an ammonium salt.

C1. A catalyst composition comprising the zeolite material of any of A1 to A11.

C2. The catalyst composition of C1, which is a substantially free of a binder.

C3. The catalyst composition of C1, further comprising a binder.

C4. The catalyst composition of C3, wherein the binder is selected from alumina, silica, titania, zirconia, zircon, kaolin, other refractory oxides and refractory mixed oxides, and mixtures and combinations thereof.

C5. The catalyst composition of C4, wherein the binder is alumina and/or silica.

C6. The catalyst composition of any of C1 to C5, having one of more of the following shapes: cylinder, solid sphere, trilobe, quadrulobe, and eggshell sphere.

C7. The catalyst composition of any of C1 to C6, further comprises a second zeolite selected from zeolites having 10- or 12-member rings in crystallite structures thereof.

C8. The catalyst composition of any of C1 to C7, further comprising a second zeolite having a constraint index in a range from 0.5 to 15, preferably from 1 to 10.

C9. The catalyst composition of any of C1 to C8, further comprising a MFI framework type zeolite.

C10. The catalyst composition of C9, wherein the MFI framework type zeolite is ZSM-5.

C11. The catalyst composition of any of C1 to C10, wherein the binder has a concentration from 0 to 90 wt %, based on the total weight of the catalyst composition, such as from 20 to 80 wt %, or from 20 to 50 wt %.

C12. The catalyst composition of any of C1 to C11, wherein the zeolite material has a concentration from 10 to 100 wt %, based on the total weight of the catalyst composition, such as from 20 to 80 wt %, or from 50 to 80 wt %.

C13. The catalyst composition of any of C1 to C12, which is for catalyzing the isomerization of C8 aromatic hydrocarbons.

D1. A process for converting a feed comprising C8 aromatic hydrocarbons, the process comprising:

(I) feeding the aromatic hydrocarbon feed into a conversion reactor; and (II) contacting the C8 aromatic hydrocarbons at least partly in a liquid phase with a conversion catalyst composition comprising a MEL framework type zeolite in the conversion reactor under conversion conditions to effect isomerization of at least a portion of the C8 aromatic hydrocarbons to produce a conversion product effluent.

D2. The process of D1, wherein the conversion catalyst composition comprises the MEL framework type zeolite at a concentration of at least 50 wt %, based on the total weight of all zeolites present in the conversion catalyst composition.

D3. The process of D1 or D2, wherein the MEL framework type zeolite is at least partly in hydrogen-form.

D4. The process of any of D1 to D3, wherein the conversion catalyst composition is the catalyst composition of any of B1 to B9.

D5. The process of any of D1 to D4, wherein the conversion conditions comprise an absolute pressure sufficient to maintain the C8 hydrocarbons in liquid phase, and one or more of:

a temperature of at most 300° C., preferably in a range from 100 to 300° C., preferably from 150 to 300° C., such as from 200 to 300° C., from 200 to 280° C., from 200 to 260° C., or from 240 to 260° C.; and a WHSV in a range from 0.5 to 20 $hour^{-1}$, preferably from 2 to 15 $hour^{-1}$, more preferably from 2 to 10 $hour^{-1}$, more preferably from 5 to 10 $hour^{-1}$.

D6. The process of any of D1 to D6, further comprising feeding molecular hydrogen into the conversion reactor.

D7. The process of D6, wherein the quantity of hydrogen fed into the conversion reactor is in a range from 4 to 250 ppm, based on the weight of the aromatic hydrocarbon feed.

D8. The process of D6 or D7, wherein the molecular hydrogen is at least partly dissolved in the liquid phase, preferably substantially completely dissolved.

D9. The process of any of D1 to D5, wherein molecular hydrogen is not fed into the conversion reactor.

D10. The process of any of D1 to D9, wherein at least one of the following is met:

(i) the feed comprises at most 1000 ppm of C9+ aromatic hydrocarbons, based on the total weight of the feed;

(ii) the feed comprises at most 10000 ppm of C7− aromatic hydrocarbons, based on the total weight of the feed; and (iii) the feed comprises at most 15 wt % of p-xylene, based on the total weight of C8 hydrocarbons in the feed.

D11. The process of any of D1 to D10, exhibiting a xylenes loss of at most 0.2% at a WHSV of at least 2.5 $hour^{-1}$, calculated as the percentage of the weight reduction of xylenes in the conversion product effluent compared to the feed, based on the total weight of xylenes in the feed.

D12. The process of any of D1 to D11, wherein the process has a WHSV of at least 2.5 $hour^{-1}$, and the process exhibits a C9+ aromatic hydrocarbons yield of at most 3000 ppm by weight, such as at most 1600 ppm, or at most 1000 ppm, based on the total weight of the conversion product effluent.

D13. The process of any of D1 to D12, wherein the process has a WHSV of at least 5.0 $hour^{-1}$, and the process exhibits a C9+ aromatic hydrocarbons yield of at most at most 1600 ppm, or at most 1000 ppm, based on the total weight of the conversion product effluent.

D14. The process of any of D1 to D13, wherein the process has a WHSV of at least 10 $hour^{-1}$, and the process exhibits a C9+ aromatic hydrocarbons yield of at most 1000 ppm, based on the total weight of the conversion product effluent.

D15. The process of any of D1 to D14, wherein the process has a WHSV of at least 2.5 $hour^{-1}$, and the process exhibits a benzene yield of at most 1000 ppm by weight, such as at most 700 ppm, or at most 500 ppm, based on the total weight of the conversion product effluent.

D16. The process of any of D1 to D15, wherein the process has a WHSV of at least 5.0 $hour^{-1}$, and the process exhibits a benzene yield of at most at most 700 ppm, or at most 500 ppm, based on the total weight of the conversion product effluent.

D17. The process of any of D1 to D16, wherein the process has a WHSV of at least 10 $hour^{-1}$, and the process exhibits a benzene yield of at most 500 ppm, based on the total weight of the conversion product effluent.

D18. The process of any of D1 to D17, wherein the process has a WHSV of at least 2.5 $hour^{-1}$, and the process exhibits a toluene yield of at most 800 ppm by weight, such as at most 500 ppm, or at most 200 ppm, based on the total weight of the conversion product effluent.

D19. The process of any of D1 to D18, wherein the process has a WHSV of at least 5.0 $hour^{-1}$, and the process exhibits a toluene yield of at most at most 200 ppm, based on the total weight of the conversion product effluent.

D20. The process of any of D1 to D19, wherein the process has a WHSV of at least 10 $hour^{-1}$, and the process exhibits a toluene yield of at most 200 ppm, based on the total weight of the conversion product effluent.

D21. The process of any of D1 to D20, wherein the aromatic hydrocarbon feed comprises p-xylene at a concentration of ≤15 wt % (preferably ≤10 wt %, preferably ≤8 wt %, preferably ≤6 wt %, preferably ≤5 wt %, preferably ≤3 wt %, preferably ≤2 wt %) based on the total weight of the xylenes in the aromatic hydrocarbon feed, and the process exhibits a p-xylene selectivity among the products of o-xylene, m-xylene, and p-xylene of at least 22% at a WHSV of 2.5 $hour^{-1}$, preferably ≥23%.

D22. The process of D21, wherein the aromatic hydrocarbon feed comprises p-xylene at a concentration ≤15 wt % (preferably ≤10 wt %, preferably ≤8 wt %, preferably ≤6 wt %, preferably ≤5 wt %, preferably ≤3 wt %, preferably ≤2 wt %) based on the total weight of the xylenes in the aromatic hydrocarbon feed, and the process exhibits a p-xylene selectivity among the products of o-xylene, m-xylene, and p-xylene of at least 20%, preferably ≥21%, preferably ≥22%, preferably ≥23%, at a WHSV of 5 $hour^{-1}$.

D23. The process of D22, wherein the aromatic hydrocarbon feed comprises p-xylene at a concentration ≤15 wt % (preferably ≤10 wt %, preferably ≤8 wt %, preferably ≤6 wt %, preferably ≤5 wt %, preferably ≤3 wt %, preferably ≤2 wt %) based on the total weight of the xylenes in the aromatic hydrocarbon feed, and the process exhibits a p-xylene selectivity among the products of o-xylene, m-xylene, and p-xylene of at least 20%, preferably ≥21%, preferably ≥22%, preferably ≥23%, at a WHSV of 10 $hour^{-1}$.

D24. The process of D23, wherein the aromatic hydrocarbon feed comprises p-xylene at a concentration ≤15 wt % (preferably ≤10 wt %, preferably ≤8 wt %, preferably ≤6 wt %, preferably ≤5 wt %, preferably ≤3 wt %, preferably ≤2 wt %) based on the total weight of the xylenes in the aromatic hydrocarbon feed, and the process exhibits a p-xylene selectivity among the products of o-xylene, m-xylene, and p-xylene of at least 20%, preferably ≥21%, at a WHSV of 15 $hour^{-1}$.

D25. The process of any of D1 to D20, wherein the feed comprising ethylbenzene in a range from 1 to 15 wt %, based on the total weight of the feed.

E1. A process for converting a feed comprising C8 aromatic hydrocarbons, the process comprising:

(I) feeding the aromatic hydrocarbon feed into a conversion reactor; and (II) contacting the C8 aromatic hydrocarbons substantially in liquid phase with a catalyst composition of any of B1 to B9 in the conversion reactor under conversion conditions to effect isomerization of at least a portion of the C8 aromatic hydrocarbons to produce a conversion product effluent, wherein the conversion conditions comprise an absolute pressure sufficient to maintain the C8 hydrocarbons in liquid phase, a temperature in the range from 150 to 300° C., and a WHSV in the range from 2.5 to 15.

E2. The process of E1, further comprising feeding molecular hydrogen into the conversion reactor at a quantity of from 4 to 250 wppm, based on the total weight of the feed, wherein the hydrogen is substantially dissolved in the liquid phase.

E3. The process of E1 or E2, wherein molecular hydrogen is not fed into the conversion reactor.

E4. The process of any of E1 to E3, wherein at least one of the following is met:

(i) the feed comprises at most 1000 ppm of C9+ aromatic hydrocarbons, based on the total weight of the feed;

(ii) the feed comprises at most 5000 ppm of C7− aromatic hydrocarbons, based on the total weight of the feed; and (iii) the feed comprises at most 15 wt % of p-xylene, based on the total weight of C8 hydrocarbons in the feed.

E5. The process of any of E1 to E4, wherein the aromatic hydrocarbon feed comprises p-xylene at a concentration no greater than 2 wt % based on the total weight of the xylenes in the aromatic hydrocarbon feed, and the process exhibits a xylenes loss of at most 0.5% at a WHSV of at least 2.5 $hour^{-1}$, calculated as the percentage of the weight reduction of xylenes in the conversion product effluent compared to the feed, based on the total weight of xylenes in the feed.

E6. The process of any of E1 to E5, wherein the aromatic hydrocarbon feed comprises p-xylene at a concentration ≤15 wt % (preferably ≤10 wt %, preferably ≤8 wt %, preferably ≤6 wt %, preferably ≤5 wt %, preferably ≤3 wt %, preferably ≤2 wt %) based on the total weight of the xylenes in the aromatic hydrocarbon feed, and the process exhibits a p-xylene selectivity among the products of o-xylene, m-xylene, and p-xylene of at least 22% at a WHSV of 2.5 $hour^{-1}$, preferably ≥23%.

E7. The process of E6, wherein the aromatic hydrocarbon feed comprises p-xylene at a concentration ≤15 wt % (preferably ≤10 wt %, preferably ≤8 wt %, preferably ≤6 wt %, preferably ≤5 wt %, preferably ≤3 wt %, preferably ≤2 wt %) based on the total weight of the xylenes in the aromatic hydrocarbon feed, and the process exhibits a p-xylene selectivity among the products of o-xylene, m-xylene, and p-xylene of at least 20%, preferably ≥21%, preferably ≥22%, preferably ≥23%, at a WHSV of 5 $hour^{-1}$.

E8. The process of E7, wherein the aromatic hydrocarbon feed comprises p-xylene at a concentration ≤15 wt % (preferably ≤10 wt %, preferably ≤8 wt %, preferably ≤6 wt %, preferably ≤5 wt %, preferably ≤3 wt %, preferably ≤2 wt %) based on the total weight of the xylenes in the aromatic hydrocarbon feed, and the process exhibits a p-xylene selectivity among the products of o-xylene, m-xylene, and p-xylene of at least 20%, preferably ≥21%, preferably ≥22%, preferably ≥23%, at a WHSV of 10 $hour^{-1}$.

E9. The process of E8, wherein the aromatic hydrocarbon feed comprises p-xylene at a concentration ≤15 wt % (preferably ≤10 wt %, preferably ≤8 wt %, preferably ≤6 wt %, preferably ≤5 wt %, preferably ≤3 wt %, preferably ≤2 wt %) based on the total weight of the xylenes in the aromatic hydrocarbon feed, and the process exhibits a p-xylene selectivity among the products of o-xylene, m-xylene, and p-xylene of at least 20%, preferably ≥21%, preferably ≥22%, preferably ≥23%, at a WHSV of 15 $hour^{-1}$.

What is claimed is:

1. A process for converting an aromatic hydrocarbon feed comprising C8 aromatic hydrocarbons, the process comprising:

(I) feeding the aromatic hydrocarbon feed into a conversion reactor; and (II) contacting the C8 aromatic hydrocarbons at least partly in a liquid phase with a conversion catalyst composition comprising a first zeolite in the conversion reactor under conversion conditions to effect isomerization of at least a portion of the C8 aromatic hydrocarbons to produce a conversion product effluent, wherein the first zeolite is of MEL framework type, wherein the conversion catalyst composition comprises a plurality of crystallites, wherein at least 75% of the crystallites have a crystallite size of at most 200 nanometers as determined by transmission electron scope image analysis, and the conversion catalyst composition comprises the MEL framework type zeolite at a concentration of at least 50 wt %, based on the total weight of all zeolites present in the conversion catalyst composition.

2. The process of claim 1, wherein the first zeolite is at least partly in hydrogen-form.

3. The process of claim 1, wherein the crystallites have an aspect ratio from 1 to 5.

4. The process of claim 1, wherein the first zeolite material have a silica to alumina molar ratio of from 10 to 60.

5. The process of claim 1, wherein the first zeolite material have a BET total surface area of from 300 to 600 $m^2/g$.

6. The process of claim 1, wherein the first zeolite material have a mesopore surface area of at least 15% of the total surface area.

7. The process of claim 1, wherein the first zeolite is calcined.

8. The process of claim 1, wherein the conversion catalyst composition further comprises a second zeolite material selected from zeolites having 10- or 12-member ring structures therein.

9. The process of claim 1, wherein the conversion conditions comprise an absolute pressure sufficient to maintain the C8 hydrocarbons in liquid phase, and one or more of:

a temperature of at most 300° C.; and a WHSV in a range from 0.5 to 20 $hour^{-1}$.

10. The process of claim 1, further comprising feeding molecular hydrogen into the conversion reactor.

11. The process of claim 10, wherein the quantity of hydrogen fed into the conversion reactor is in a range from 4 to 250 ppm, based on the weight of the aromatic hydrocarbon feed.

12. The process of claim 1, wherein molecular hydrogen is not fed into the conversion reactor.

13. The process of claim 1, exhibiting a xylenes loss of at most 0.2% at a WHSV of at least 2.5 $hour^{-1}$, calculated as the percentage of the weight reduction of xylenes in the conversion product effluent compared to the aromatic hydrocarbon feed, based on the total weight of xylenes in the aromatic hydrocarbon feed.

14. The process of claim 1, wherein the process has a WHSV of at least 2.5 $hour^{-1}$, and the process exhibits a C9+ aromatic hydrocarbons yield of at most 3000 ppm by weight, based on the total weight of the conversion product effluent.

15. The process of claim 1, wherein the process has a WHSV of at least 5.0 $hour^{-1}$, and the process exhibits a C9+ aromatic hydrocarbons yield of at most at most 1600 ppm, based on the total weight of the conversion product effluent.

16. The process of claim 1, wherein the process has a WHSV of at least 10 $hour^{-1}$, and the process exhibits a C9+ aromatic hydrocarbons yield of at most 1000 ppm, based on the total weight of the conversion product effluent.

17. The process of claim 1, wherein the aromatic hydrocarbon feed comprises p-xylene at a concentration ≤15 wt % based on the total weight of the xylenes in the aromatic hydrocarbon feed, and the process exhibits a p-xylene selectivity among the products of o-xylene, m-xylene, and p-xylene of at least 20%.

18. The process of claim 1, wherein the aromatic hydrocarbon feed comprises p-xylene at a concentration ≤15 wt % based on the total weight of the xylenes in the aromatic hydrocarbon feed, and the process exhibits a p-xylene selectivity among the products of o-xylene, m-xylene, and p-xylene of at least 20%.

19. A process for converting an aromatic hydrocarbon feed comprising C8 aromatic hydrocarbons, the process comprising:

(I) feeding the aromatic hydrocarbon feed into a conversion reactor; and (II) contacting the C8 aromatic hydrocarbons substantially in liquid phase with a conversion catalyst composition in the conversion reactor under conversion conditions to effect isomerization of at least a portion of the C8 aromatic hydrocarbons to produce a conversion product effluent, wherein the conversion conditions comprise an absolute pressure sufficient to maintain the C8 hydrocarbons substantially in liquid phase, a temperature in the range from 150 to 300° C., and a WHSV in the range from 2.5 to 20 $hour^{-1}$, wherein the conversion catalyst composition comprises a first zeolite material of the MEL framework type, the first zeolite material has a silica to alumina molar ratio in the range from 20 to 40 and comprises a plurality of crystallites, at least 75% of the crystallites have crystallite size of at most 200 nanometers as determined by transmission electron scope image analysis, and the conversion catalyst composition comprises the MEL first zeolite at a concentration of at least 50 wt %, based on the total weight of all zeolites present in the conversion catalyst composition.

20. The process of claim 19, wherein the first zeolite material has a silica to alumina molar ratio from 20 to 30.

21. The process of claim 19, further comprising feeding molecular hydrogen into the conversion reactor at a quantity of from 4 to 250 wppm, based on the total weight of the feed, wherein the hydrogen is substantially dissolved in the liquid phase.

22. The process of claim 19, wherein molecular hydrogen is not fed into the conversion reactor.

* * * * *